United States Patent

Andrevski et al.

[11] Patent Number: 5,882,903
[45] Date of Patent: Mar. 16, 1999

[54] ASSAY SYSTEM AND METHOD FOR CONDUCTING ASSAYS

[75] Inventors: Zygmunt M. Andrevski, Princeton; William Ronald Roach, Rocky Hill; Peter David Southgate, Monmouth Junction; Peter John Zanzucchi, Lawrenceville, all of N.J.

[73] Assignee: Sarnoff Corporation, Princeton, N.J.

[21] Appl. No.: 742,317

[22] Filed: Nov. 1, 1996

[51] Int. Cl.⁶ .............. C12P 19/34; C12M 1/00; G01N 21/29

[52] U.S. Cl. .............. 435/91.2; 435/91.1; 435/287.2; 435/287.3; 422/50; 422/55; 422/63; 422/64; 422/68.1; 422/82.05; 422/82.17; 422/99

[58] Field of Search ................ 422/50, 55, 58, 422/62, 63, 64, 67, 68.1, 82.05, 82.12, 99; 435/286.5, 287.1, 287.2, 287.3; 935/85

[56] References Cited

U.S. PATENT DOCUMENTS

| | | | |
|---|---|---|---|
| 3,889,151 | 6/1975 | Hanak et al. | 315/170 |
| 4,399,361 | 8/1983 | Zanzucchi et al. | 250/341 |
| 5,176,203 | 1/1993 | Larzul | 165/61 |
| 5,229,580 | 7/1993 | Chioniere | 219/521 |
| 5,364,790 | 11/1994 | Atwood et al. | 435/288 |
| 5,415,839 | 5/1995 | Zaun et al. | 422/64 |
| 5,422,271 | 6/1995 | Chen et al. | 435/287 |
| 5,451,500 | 9/1995 | Stapleton | 435/6 |
| 5,460,780 | 10/1995 | Devaney, Jr. et al. | 422/99 |
| 5,475,610 | 12/1995 | Atwood et al. | 364/500 |
| 5,585,069 | 12/1996 | Zancucchi et al. | 422/100 |
| 5,593,838 | 1/1997 | Zanzucchi et al. | 435/6 |
| 5,602,756 | 2/1997 | Atwood et al. | 364/500 |
| 5,616,301 | 4/1997 | Moser et al. | 422/104 |
| 5,643,738 | 7/1997 | Zanzucchi et al. | 435/6 |
| 5,654,200 | 8/1997 | Copeland et al. | 436/46 |

OTHER PUBLICATIONS

ERICOMP PowerBlock System (advertisement), PCR Methods and Applicaitons, vol. 3, No. 2, Oct. 1993.

International Search Report on corresponding International Application No. PCT/US96/17116.

*Primary Examiner*—Bradley L. Sisson
*Attorney, Agent, or Firm*—William J. Burke

[57] ABSTRACT

The invention relates to an assay system for conducting elevated temperature reactions in a fluid-tight manner within a reaction chamber, the assay system comprising: (a) a first assembly comprising the reaction chamber, and (b) a second assembly for temperature control, wherein the second assembly can be positioned adjacent to the reaction chamber. More particularly, the invention relates to an assay system comprising (a) a reaction chamber having a cover formed of a deformable material and (b) a mechanism for rapidly adjusting the temperature of the reaction chamber.

27 Claims, 11 Drawing Sheets

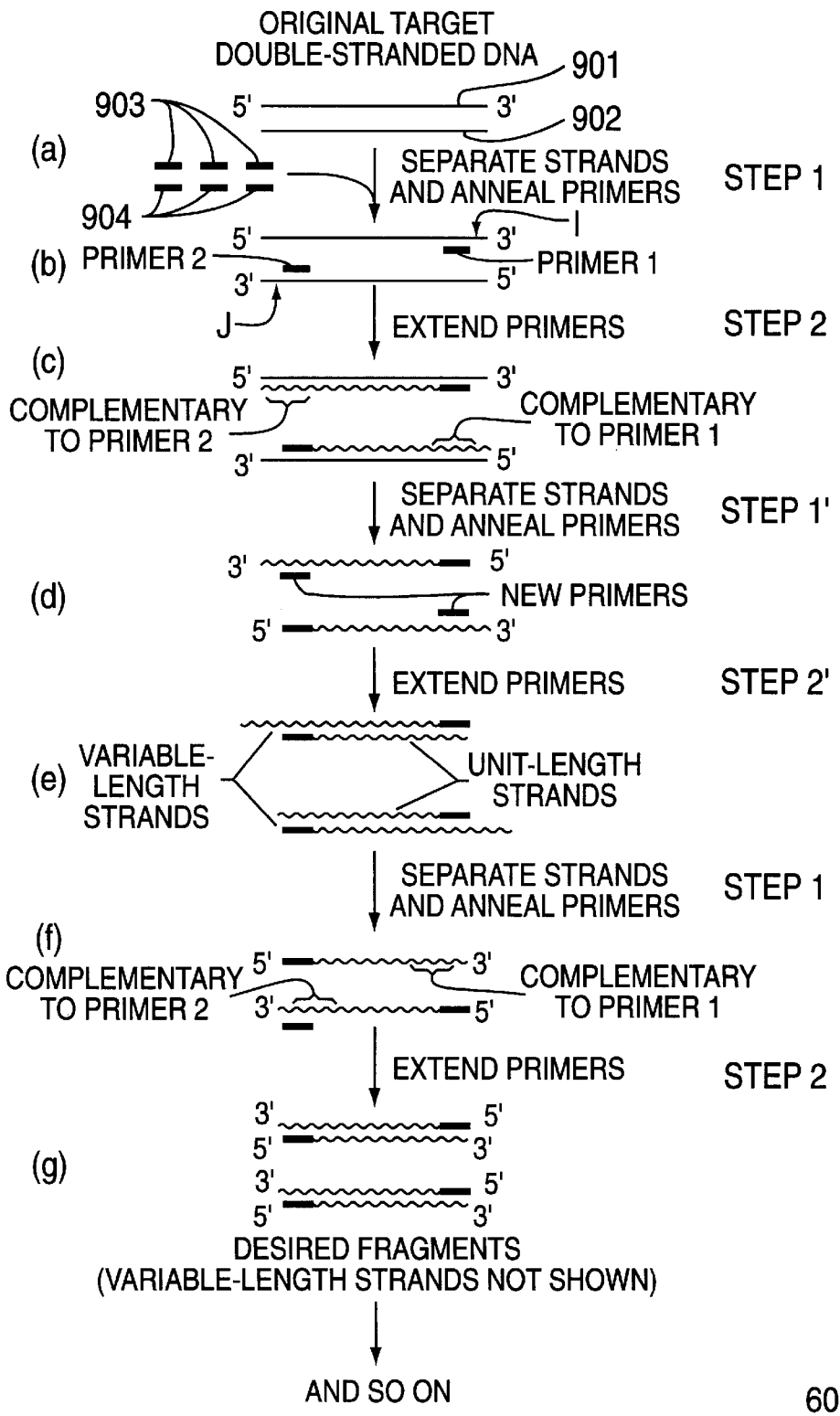
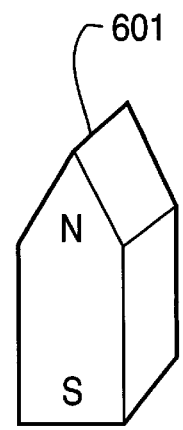
FIG. 9
FIG. 10

ASSAY SYSTEM AND METHOD FOR CONDUCTING ASSAYS

The invention was made with U.S. Government support under Contract No. 70NANB5H1037. The U.S. Government has certain rights in this invention.

The invention relates to the field of scientific chemical assays and, in particular, to a system and method for conducting such assays.

Scientific assays useful in criminal forensics and medical diagnostics, for example, have increasingly involved biochemical procedures, such as the polymerase chain reaction ("PCR") which has proven to be very valuable for analysis of trace amounts of DNA. In particular, the PCR assay has provided a powerful method of assaying for the presence of either defined segments of nucleic acids or segments that are highly homologous to such defined segments. The method can be used to assay body fluids for the presence of nucleic acid specific for particular pathogens, such as the mycobacterium causing Lyme disease, the HIV virus or any other pathogenic microbe. The microbe diagnostic assay functions by adding, to a sample that may contain a target segment of nucleic acid from the microbe's genome, two "primers" (i.e., relatively short nucleic acid segments or nucleic acid analogs) that specifically bind to (i.e., "hybridize" with) the target segment of nucleic acid. The first primer binds to a first strand of the two-stranded target nucleic acid segment and, when hybridized, can prime the enzymatic reproduction of a copy of the second strand of the target nucleic acid segment in a direction arbitrarily designated as the downstream direction. The second primer binds to the second strand of the target nucleic acid segment at a position downstream from the first primer hybridization site and can prime the enzymatic reproduction of a copy of the first strand of the target nucleic acid segment in the upstream direction. (In the case where the sample is made up of single-stranded target nucleic acids, the second primer will hybridize with the theoretical second strand determined with the Watson-Crick base-pairing rules.) To the sample are added the monomer building blocks of nucleic acid and an enzyme that specifically catalyzes nucleic acid reproduction from a single strand of nucleic acid to which a short primer is bound. The enzyme is preferably highly resistant to destruction by high temperatures. The sample is heated to a DNA melting temperature to separate the two strands of the sample nucleic acid and then cooled to a replication temperature. The replication temperature allows the primers to specifically bind to the separated strands and allows the reproductive enzyme to operate. After this cycle, the reaction mix contains two sets of the two stranded nucleic acid segment for each target nucleic acid segment that was originally present. Heating and replication temperature cycles are repeated until sufficient amounts of the nucleic acid segment are created through this exponential reproduction method. For instance, after 20 cycles the segment has been amplified as much as $2^{20}$-fold, or roughly 1,000,000-fold. The PCR process is diagrammed in FIG. 9.

There are several problems associated with automating the PCR reaction. First, the degree of amplification achieved by the assay creates a large risk of contamination from inadvertently mixed samples or oligonucleotides bound to laboratory equipment. Thus far, this risk has been dealt with in commercial or manual procedures by conducting the reactions in "clean" facilities that are extremely expensive to construct and maintain. For automation, this risk implies that all the reagents needed and the reaction chamber for the amplification should be contained in a disposable platform in which the sample can be inserted in a controlled, one-time operation and that sample preparation steps should be minimized and, to the extent possible, conducted within a disposable platform.

Second, the high temperatures needed to "melt" the nucleic acid so that the two strands separate imply that the reaction chamber must be well-sealed against vapor loss, even while allowing the insertion and removal of various reagent fluids.

Third, the reactions should be conducted in relatively small volumes, generally volumes of no more than about 100 $\mu$l, to conserve expensive reagents and minimize the amount of sample, which could be a precious sample fluid or tissue that must be conserved to allow for other types of testing or only available in a small amount.

The invention provides a solution to the difficulties presented by current methods by providing a small-scale, disposable device that has effective, fluid-tight valves for controlling the insertion into and evacuation out of the reaction chamber of fluids.

SUMMARY OF THE INVENTION

The invention is an assay system for conducting elevated temperature reactions in a fluid-tight manner within a reaction chamber, where the assay system comprises a first assembly comprising the reaction chamber, and a second assembly for temperature control, wherein the second assembly can be positioned adjacent to the reaction chamber.

The invention is also a method of conducting a PCR reaction comprising introducing a sample into a first reaction chamber of the assay system of the invention and transferring from one or more fluid chambers to the first reaction chamber solutions containing reagents necessary for conducting the PCR reaction.

BRIEF DESCRIPTION OF THE DRAWING

The teachings of the invention can be readily understood by considering the following detailed description in conjunction with the accompanying drawing, in which:

FIG. 9 schematically diagrams the first two cycles of a PCR reaction.

FIG. 10 shows an example of a magnet useful in providing stirring for the reaction chambers.

To facilitate understanding, identical reference numerals have been used, where possible, to designate identical elements that are common to the Figures.

DEFINITIONS

Figure 1A:
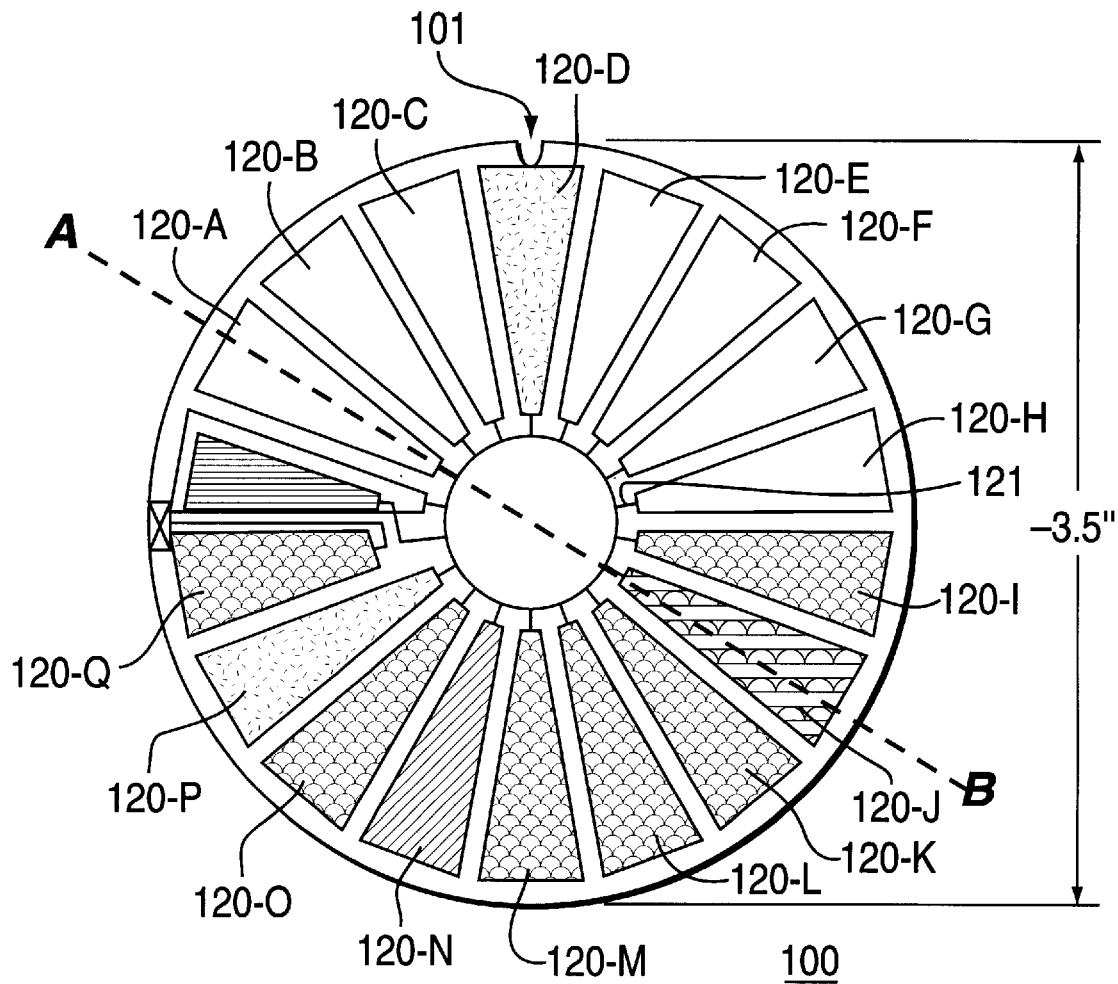
FIG. 1A displays a top view of the bottom tray of a carousel of the invention.

The following terms shall have the meanings set forth below:

"annealing temperature" means about 5° C. below the lowest $T_m$ for one of the primers used in a PCR reaction and the target nucleic acid segment. PCR protocols often use an annealing temperature less than the replication temperature to accelerate the rate at which the primers bind to (i.e., hybridize with) the sample nucleic acid; this temperature is typically between about 45° C. and about 72° C., often about 55° C.

"DNA strand separation temperature" means the temperature used in a PCR protocol to separate the complementary strands of nucleic acid that may be present in a sample; this temperature is typically between about 92° C. and about 97° C., preferably about 94° C.

"elevated pressure" means a pressure more than ambient atmospheric pressure.

"first assembly" means an assembly that includes at least one reaction chamber, at least one fluid exchange channel, and at least one fluid exchange port; wherein the first assembly can form fluid-tight connection with a suitable third assembly.

"fluid-tight" means the characteristic of a space that retains the mass of an aqueous fluid filling the space and heated to a temperature of 90° C. to 100° C. for one hour; a seal between two materials is fluid-tight if the seal is substantially no more permeable to water than the most permeable material.

"nucleic acid melting temperature" or "$T_m$" means the transition temperature for two-stranded duplex of nucleic acid at which the equilibria shifts from favoring the base-paired duplex to favoring the separation of the two strands.

"reaction cassette" means a disposable unit comprising a first assembly and a third assembly.

"reduced pressure" means a pressure that is less than ambient atmospheric pressure.

"replication temperature" means the temperature used in PCR to allow the nucleic acid reproductive enzyme to reproduce the complementary strand of a nucleic acid to which a primer is bound (i.e., hybridized); this temperature is typically between about 69° C. and about 78° C., preferably about 72° C., when using a heat stable polymerase such as Taq polymerase.

"second assembly" means an assembly for controlling temperature that includes a heat source or a cooling sink or both; the second assembly is also referred to herein as an "auxiliary block," and can include a fluid impeller.

"substantially uniform temperature" means a temperature that varies by no more than about +/-0.3° C.

"target nucleic acid segment" means a segment of nucleic acid that is sought to be identified or measured in a sample of nucleic acid, such as a sequence intended, if present, to be amplified in a PCR reaction; the target segment is typically part of a much larger nucleic acid molecule found in the sample.

"third assembly" means an assembly that includes one or more fluid chambers, one or more fluid exchange channels and ports, and which can form a fluid-tight combination with a suitable first assembly.

DETAILED DESCRIPTION

The invention is an assay system for conducting biochemical reactions in a fluid-tight manner within a reaction chamber. The assay system is not limited by any particular geometry or configuration of its component parts; preferably, the assay system includes circular, square, or rectangular assemblies, or combinations thereof, such that separate components that respectively comprise a reaction chamber ("a first assembly"), a heat source or a cooling sink or both ("a second assembly"), and a plurality of fluid chambers ("a third assembly") can move with respect to each other by sliding or translocating, as appropriate. The first and third assemblies may each have an adjoining edge or surface that has fluid exchange ports that can reversibly connect to provide fluid communication between the assemblies as a result of the sliding of one assembly with respect to the other along the adjoining edge or surface. Such sliding occurs in a linear or circular manner depending on the configuration of the assemblies that is used; if a circular configuration is used, such sliding is alternaitively referred to as rotating. The first and second or first and. third assemblies or both may also each have an adjoining surface or surfaces that can reversibly be placed in contact with one another to provide temperature control, or fluid impelling to or from fluid or reaction chambers, or both, as a result of the translocation of the second assembly to contact or separate from the first or third or both assemblies.

Figure 1B:
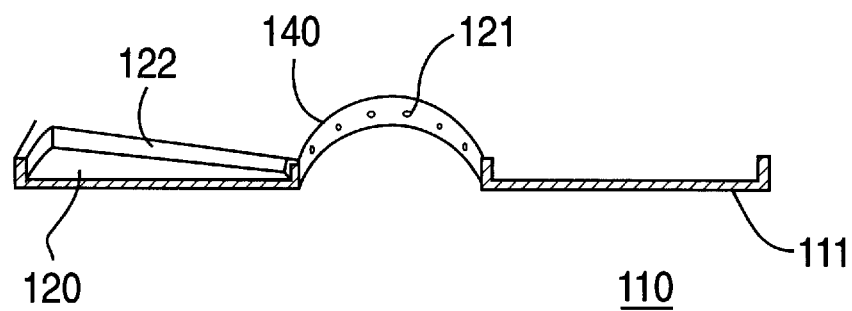
FIG. 1B displays a cut-away, perspective view of the bottom tray illustrated in FIG. 1A, the cut-away is along axis A–B shown in FIG. 1A.

A circular embodiment has been drawn and presented in the accompanying Figures. In FIGS. 1A and 1B, the bottom tray 110 of a carousel 100 is shown that has 18 fluid chambers 120A–Q. Each chamber 120 has a fluid exchange port 121 that is or can be in communication with fluid exchange channels. In the carousel 100, the sidewalls 122 of the chambers are molded together with the base 111 of the carousel 100, which base 111 forms the bottom 123 of each chamber 120A–Q. Each fluid exchange port 121A–Q exits at the smooth inner ring surface 140 formed by the carousel 100. Not illustrated is the top cover 130 of the carousel 100 that fits on top of bottom tray 110. The cover 130 will generally cover the fluid chambers, and the junction between the top of the sidewalls 122 and the cover 130 will generally form a fluid-tight seal. Also illustrated is position notch 101, which serves to interact with the mechanism controlling the assay system to identify the rotational position of the carousel 100.

Figure 2A:
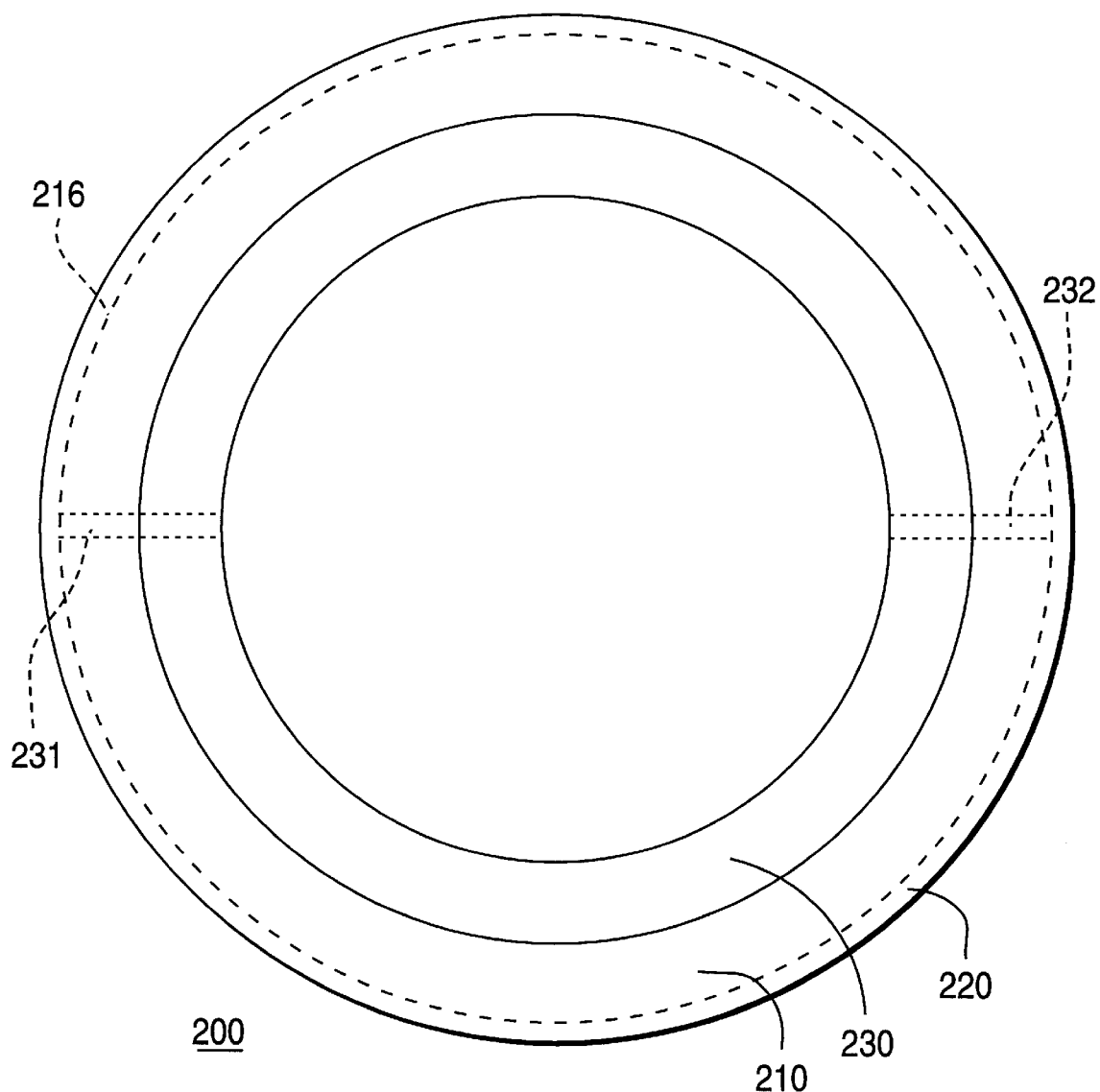
FIG. 2A shows a top view of a reaction chamber disk.
Figure 2B:
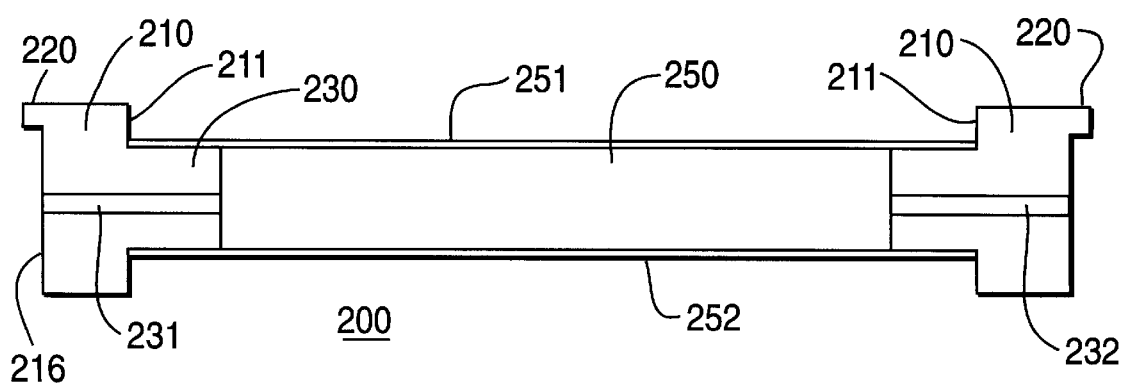
FIG. 2B shows a cut-away side view of the reaction chamber disk of FIG. 2A.

FIGS. 2A and 2B show the superstructure of a reaction chamber disk 200, which is a design that can fit with any system geometry provided that a circular slot is provided for insertion of the reaction chamber disk. For example, the disk 200 illustrated in FIGS. 2A and 2B can be used in conjunction with the carousel 100. Alternatively, the reaction chamber disk could be used in conjunction with a rectangular assembly that comprised a plurality of fluid chambers and included a suitable circular slot for insertion of the reaction chamber disk. The disk 200, comprised of one or more reaction chambers, is one embodiment of a first assembly of the assay system. Alternatively, the first assembly can be any other suitable shape that provides ability to effect or break communication via fluid exchange channels included in the first assembly with those in a third assembly that provides reagents and waste disposal from or to fluid chambers.

Figure 2C:
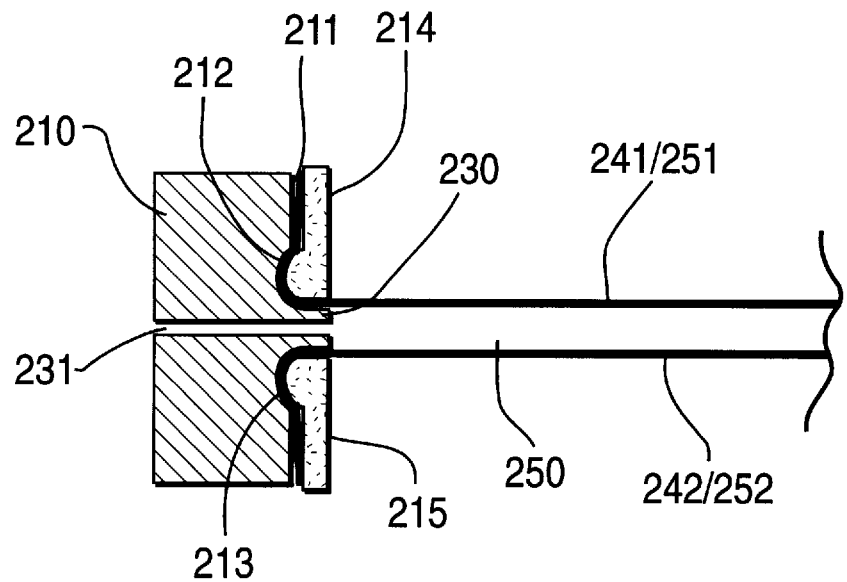
FIGS. 2C and 2D show an enlarged view of the sidewall of a reaction chamber disk.
Figure 2D:
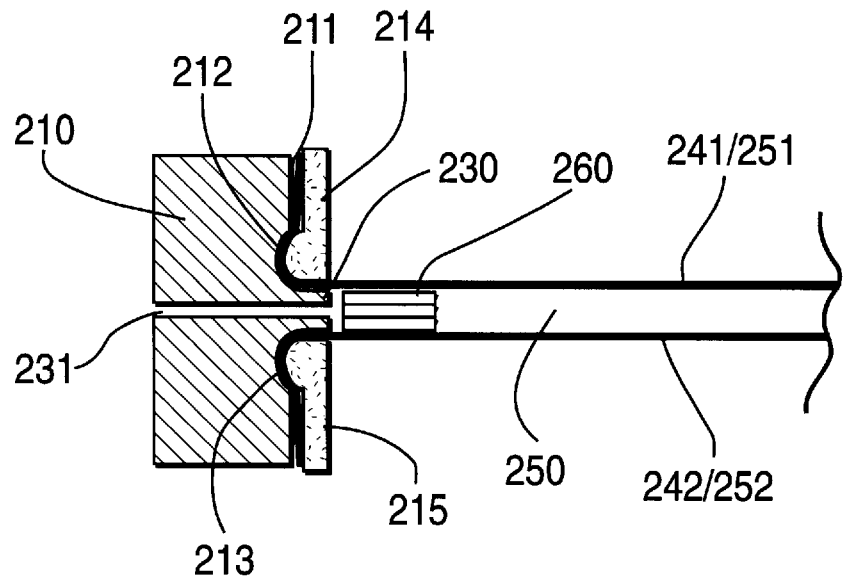

The first assembly, embodied as disk 200, includes a structural ring 210, a bevel edge 220 and a spacer ring 230 that defines the width of the reaction chamber. First fluid exchange channel 231 and second fluid exchange channel 232 are located on opposite sides of disk 200. In FIG. 2C, the sidewalls 211 of ring 210 has first and second notches 212 and 213. First and second locking rings 214 and 215, shown in cross-section, lock into place within ring 210 by clipping into notches 212 and 213, respectively. Membrane 241 fits between first locking ring 214 and first notch 212, thereby creating an upper cover 251 for reaction chamber 250. Membrane 242 similarly fits between second locking ring 215 and second notch 213 to form lower cover 252. Smooth outer surface 216 fits snugly against inner ring surface 140 of the carousel 100 to form a fluid-tight seal, thus forming a snug junction. A "snug junction" is one that is fluid-tight. In FIG. 2D, the disk 200 further includes a gasket 260 that serves to insulate spacer ring 230 and ring 210 from the elevated temperatures of the chamber 250.

Figure 3:
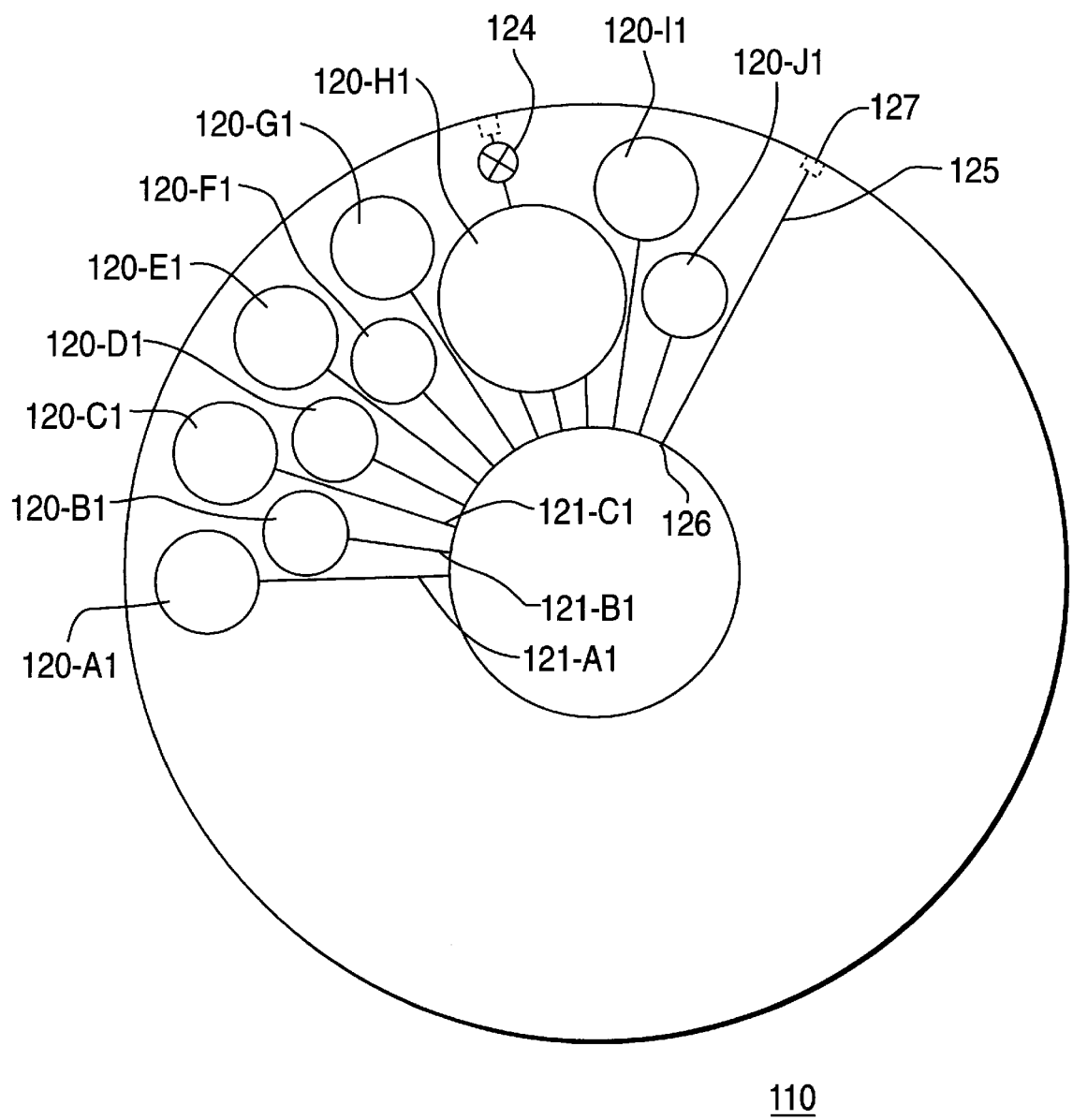
FIG. 3 shows a top view of another bottom tray of a carousel.

FIG. 3 illustrates another embodiment of tray 110. In addition to the features identified above, the carousel 100 has conduits 125, having first opening 126 and second opening 127. Conduits are also referred to herein as fluid exchange channels. Second opening 127 is designed to facilitate a union with a source of a gas or liquid (not illustrated). Fluid chamber 120-H1 is connected to the outer rim of the carousel by valved portal 124.

Figure 4A:
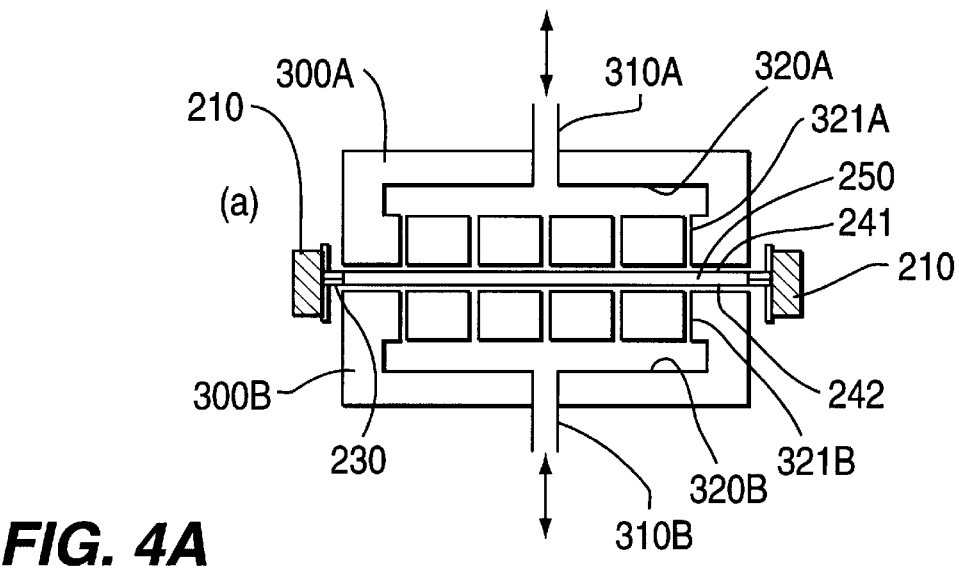
FIG. 4A illustrates an apparatus for forcing fluids into or out of a reaction chamber.
Figure 4B:
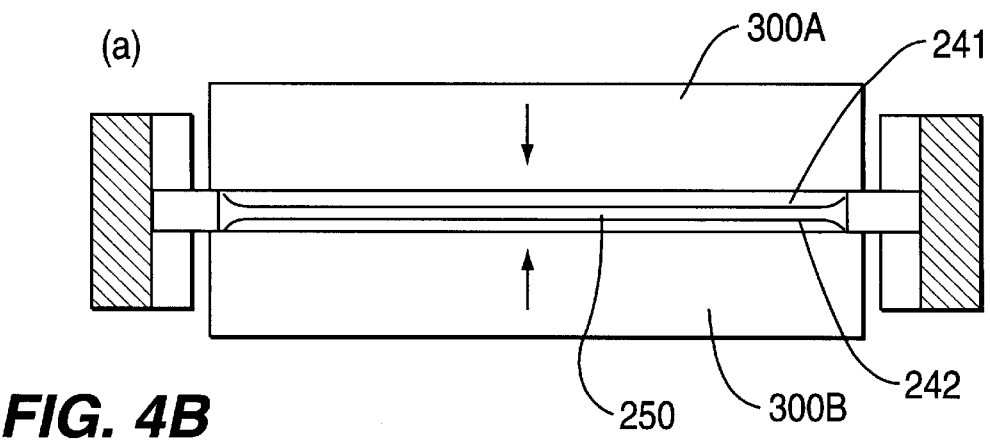
FIGS. 4B and 4C illustrate the operation of the apparatus of FIG. 4A.
Figure 4C:
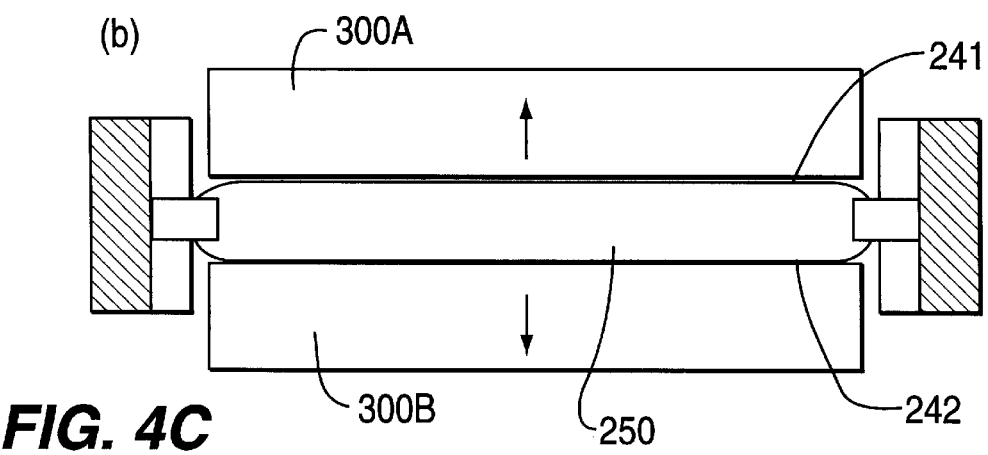

FIGS. 4A, 4B and 4C illustrate a mechanism having upper auxiliary block 300A and lower auxiliary block 300B for forcing fluids into the chamber 250, wherein the assay system has any suitable geometry and structure 300 is an embodiment of a fluid impeller. Upper block 300A is honeycombed with passageways including upper gas inlet/outlet 310A, upper manifold 320A and a plurality of upper pressurized channels 321A. Upper channels 321A exit adjacent to the surface of upper membrane 241. The corresponding structures of the symmetrical lower block 300B are correspondingly numbered using the suffix "B" instead of "A". In FIG. 4B, gas pressure has been applied through upper gas inlet/outlet 310A and lower gas inlet/outlet 310B, so that gas exiting upper and lower pressurized channels 321A and 321B forces upper and lower membranes 241 and 242 together, thereby forcing fluid from chamber 250, thus providing explanation of the aforementioned fluid impeller embodiment. In FIG. 4C, a vacuum applied to gas inlet/outlets 310A and 310B creates suction at upper and lower channels 321A and 321B, causing the upper and lower membranes 241 and 242 to adhere to blocks 300A and 300B, respectively, thereby pulling upper and lower membranes 241 and 242 apart and partially evacuating the invention. The partial vacuum in chamber 250 helps draw fluid into the invention through one of first or second fluid exchange channels 231 or 232.

Figure 5:
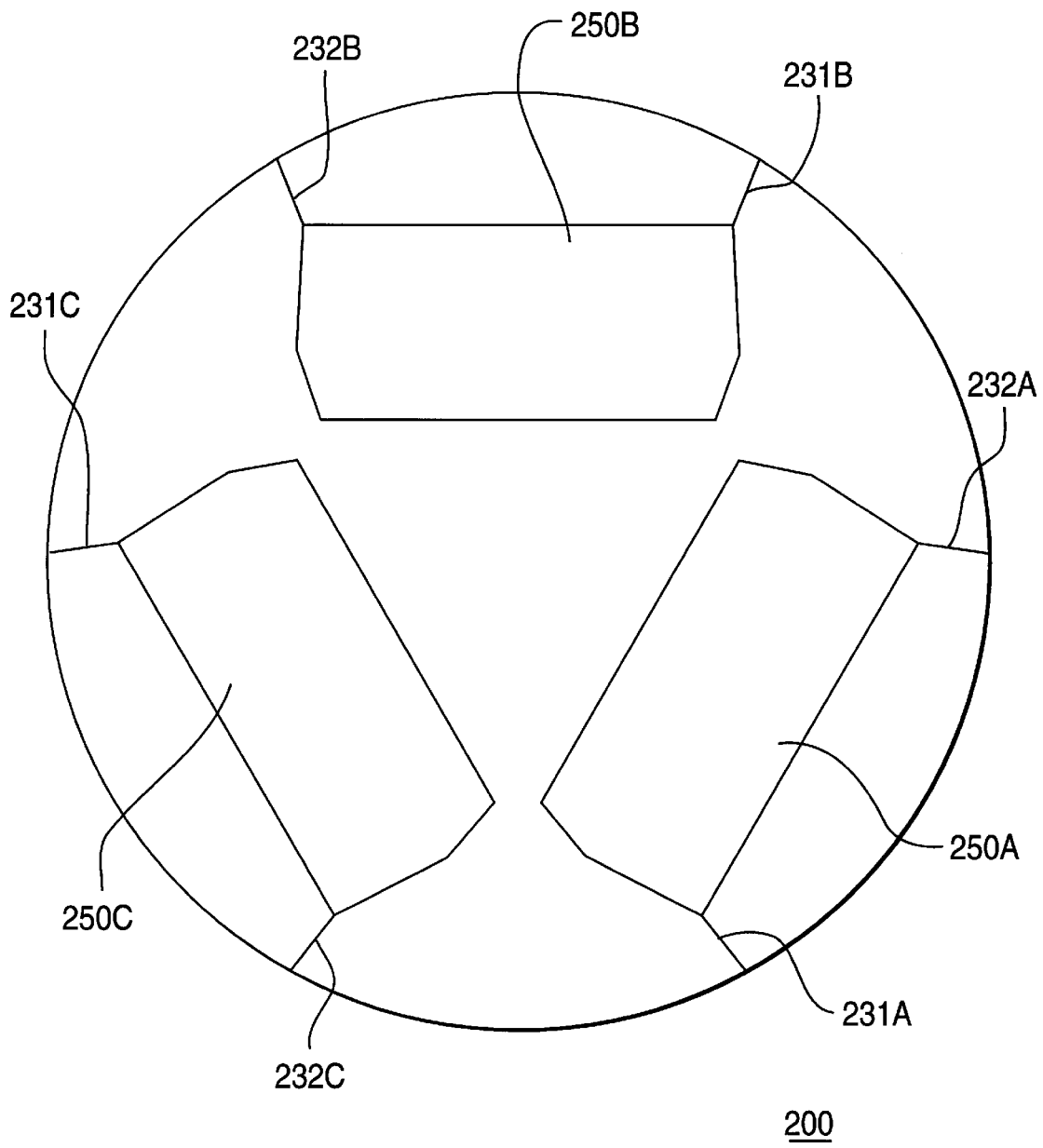
FIG. 5 shows a reaction chamber disk that includes three reaction chambers.

In FIG. 5, the reaction chamber disk 200 includes three chambers 250A–250C, which can be any suitable shape or volume, each with its own set of first fluid exchange channels 231A–231C and second fluid exchange channels 232A–232C.

Figure 6A:
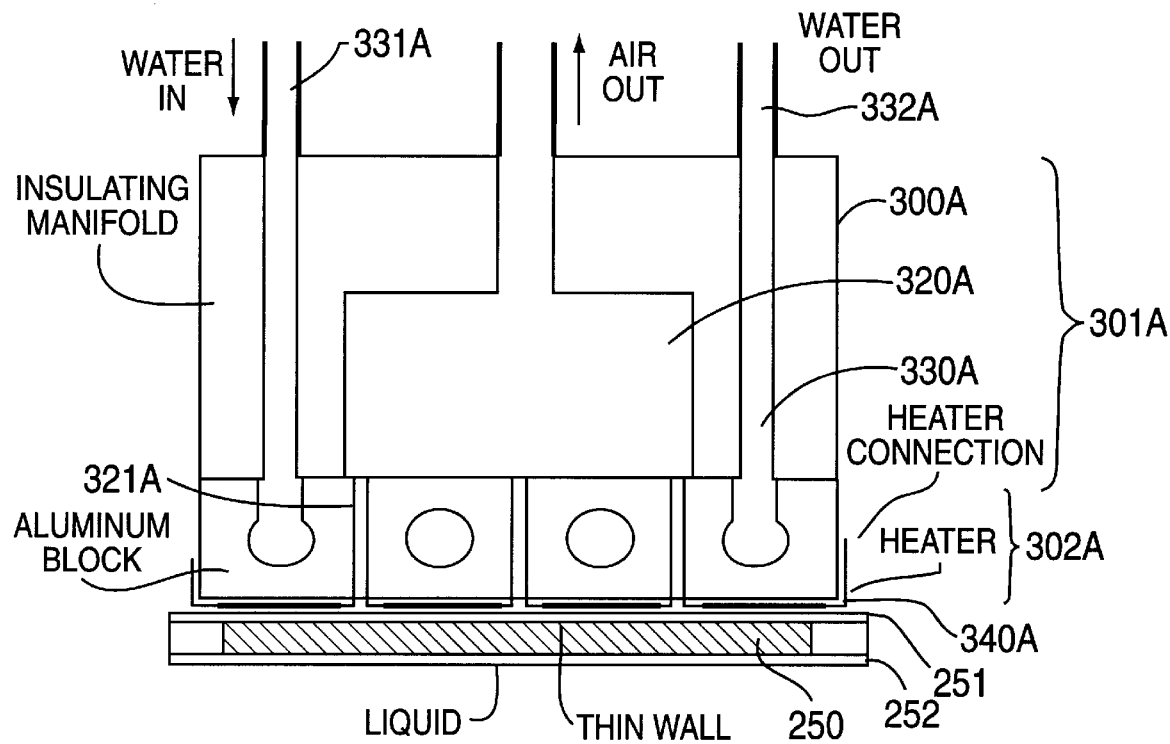
FIGS. 6A, 6B and 6C show a mechanism for rapidly heating or cooling the reaction chamber.

FIG. 6A shows one embodiment of a second assembly which is similar to the auxiliary block illustrated in FIGS. 4A–4C, except that it includes additional features. The second assembly 300A is honeycombed with upper conduit 330A. Upper conduit 330A has an upper inlet 331A and an upper outlet 332A. Upper portion 301A of upper block 300A is fabricated of a heat-insulating material, while upper section 302A is fabricated of a heat-conductive material. Upper electrical heaters 340A are positioned adjacent to the chamber 250. Generally, a duplicate lower second assembly 300B of the illustrated upper second assembly 300A is positioned beneath the chamber 250.

Figure 6B:
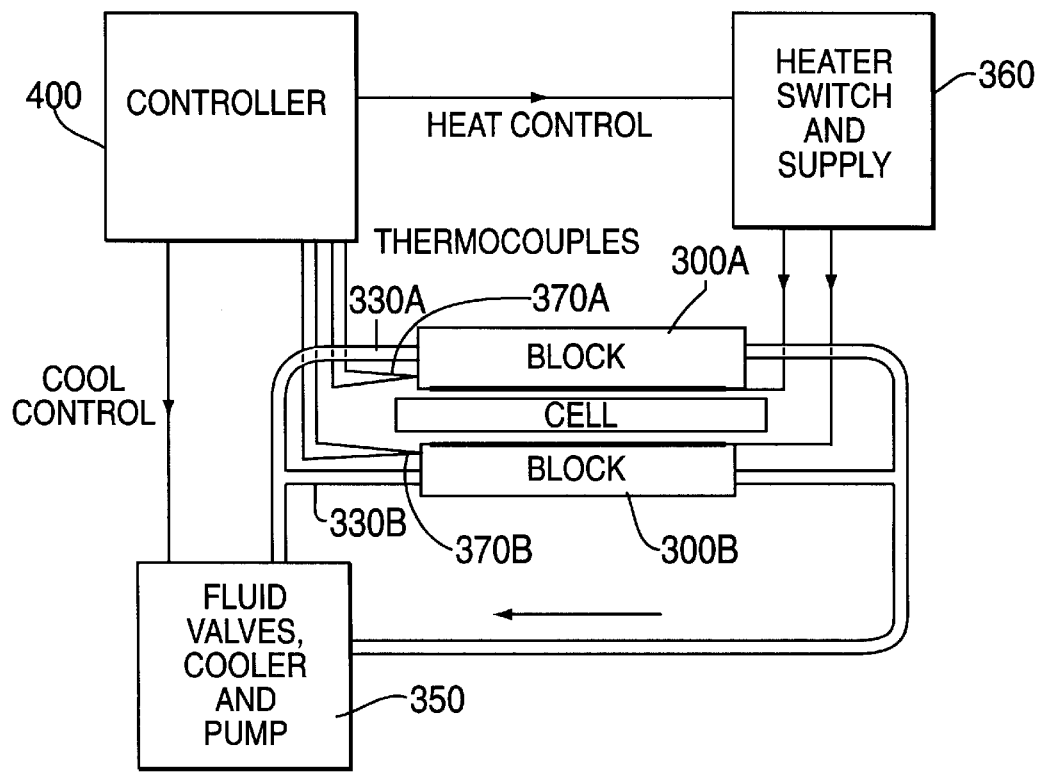

FIG. 6B shows a schematic of the accessory support devices for the upper second assembly 300A of FIG. 6A. Chilled water is propelled through upper and lower conduits 330A and 330B from pump and water cooler console 350. Pump and water cooler console 350 further includes fluid valves operating under the control of controller 400. Electrical current is supplied to upper and lower heaters 340A and 340B by power supply 360, which is controlled by controller 400. Controller 400 receives input from upper and lower thermal sensors 370A and 370B.

Figure 6C:
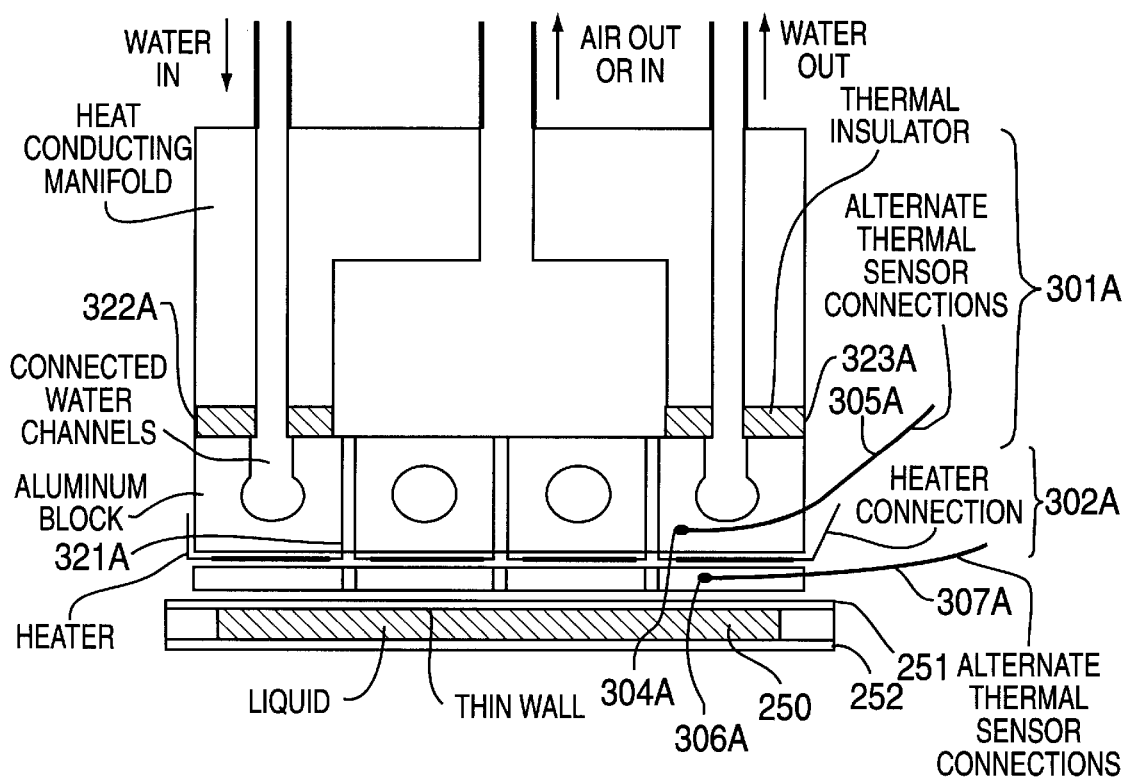

FIG. 6C shows another embodiment of a second assembly 300A similar to that of FIG. 6A, except that an upper extension 303A is added to the outer face of the upper auxiliary block 300A. The upper extension 303A is generally fabricated of the same material as upper section 302A. The upper portion 301A can favorably be fabricated of the same material as upper section 302A. First and second upper thermal insulator segments 322A and 323A are interposed between upper portion 301A and upper section 302A. First and second upper thermal sensors 304A and 306A are located in upper section 302A and upper extension 303A, respectively, and are connected to controller 400 by first and second upper leads 305A and 307A, respectively.

Figure 7A:
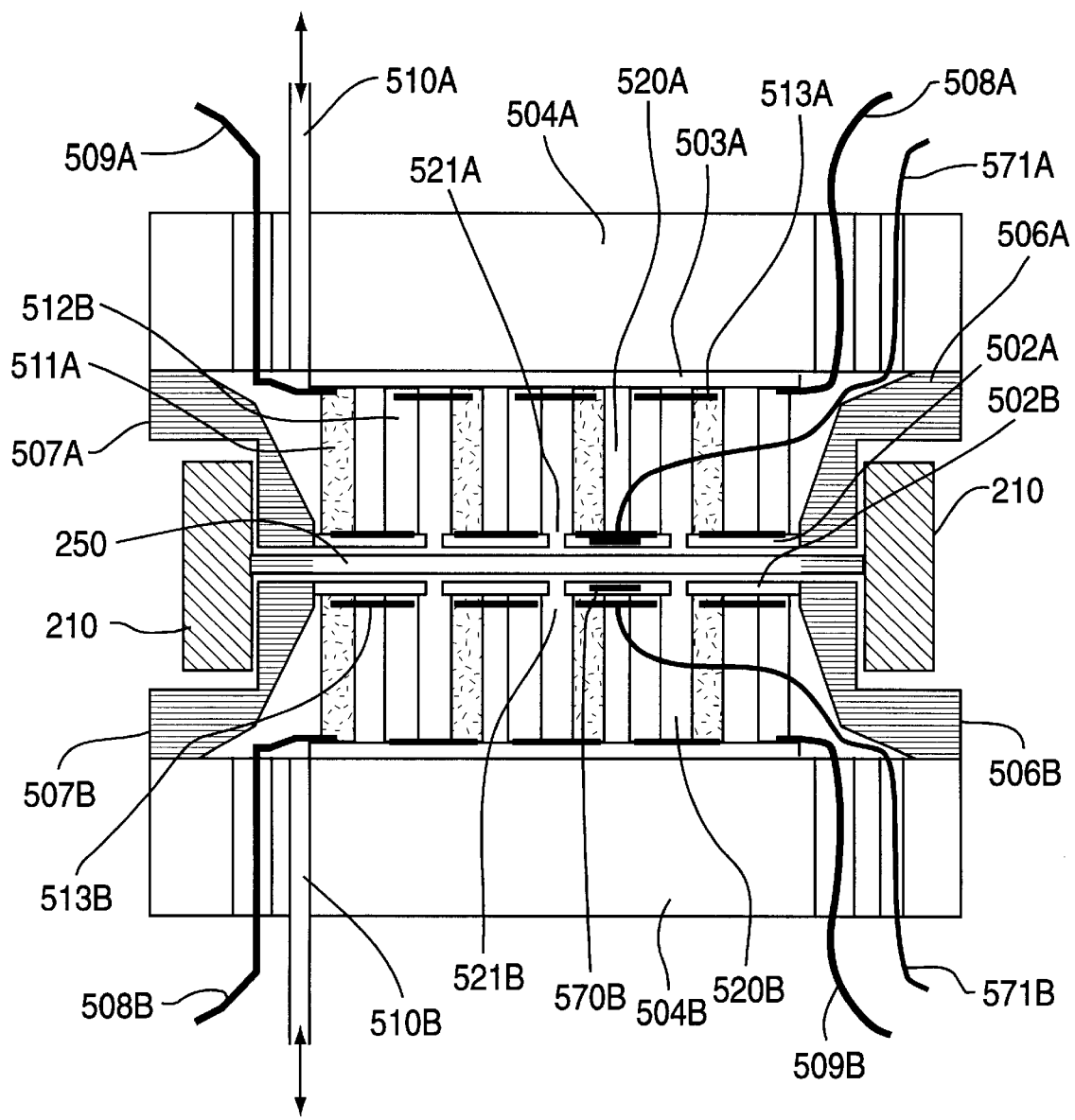
FIGS. 7A and 7B show another mechanism for rapidly heating or cooling the reaction chamber.
Figure 7B:
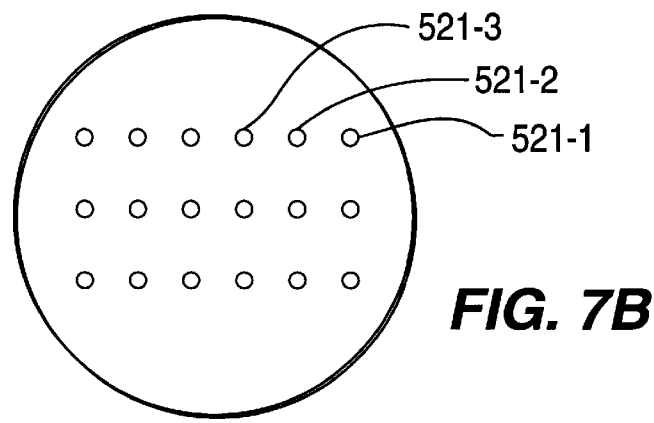

In FIG. 7A, an upper second assembly 500A includes a set of paired first and second upper thermoelectric blocks 511A and 512A, while lower second assembly 500B has a set of paired first and second lower thermoelectric blocks 511B and 512B. First upper and lower thermoelectric blocks 511A and 511B are made of p-type semiconductor material, while second upper and second lower thermoelectric blocks 512A and 512B are made of n-type semiconductor material. The blocks 511 and 512 are electrically connected in series by upper and lower connectors 513A and 513B to form thermoelectric heat pumps. Upper and lower gas inlet/outlets 510A and 510B are connected to upper and lower manifolds 520A and 520B, respectively, formed by the space between the upper and lower thermoelectric blocks 501A and 501B. Manifolds 520A and 520B are connected, respectively, to an upper plurality of passageways 521A or a lower plurality or passageways 521B. The outer portions of upper and lower blocks 500A and 500B are upper and lower heat sinks 504A and 504B, respectively. First upper air-tight collar 506A, second upper air-tight collar 507A, first lower air-tight collar 506B and second lower air-tight collar 507B help form manifolds 520A and 520B. Upper and lower thermal sensors 570A and 570B are connectable to a controller or a monitoring device by upper and lower leads 571A and 571B, respectively. FIG. 7B illustrates the surface of a ceramic end-plate 502 that would face the chamber 250. FIG. 7B illustrates one of the three dimensional aspects of second assemblies 500A and 500B not apparent in FIG. 7A; another attribute of the second assemblies not apparent in FIG. 7A is that the thermoelectric blocks will typically be arrayed in three dimensions rather than two, as illustrated.

FIG. 9 shows a schematic of a polymerase chain reaction. Line 901 represents a first strand of target DNA having, from right to left, 5' to 3' orientation. Line 902 represents the complementary strand of target DNA having 3' to 5' orientation. Primers 903 are complementary to first strand 901 at position I. Primers 904 are complementary to second strand 902 at position J. A temperature stable DNA polymerase (e.g. Taq polymerase) and the nucleotide triphosphates used by the polymerase to replicate DNA are present in the mixture. As a first step, the temperature is raised to a strand separation temperature to separate strands 901 and 902. Then, in a second step, the temperature is lowered to a replication temperature where the abundant primers bind to the first and second strands 901 and 902, respectively, at positions I and J, respectively, and the polymerase builds onto the bound first and second primers 903 and 904 to construct replicas of portions of first strand 902 and second strand 901, respectively. After two cycles, the portion of DNA between the positions I and J has been replicated four-fold.

The chamber 250 can have any suitable shape. For a circular shape, the aforementioned third assembly preferably is in the shape of a carousel, i.e., a circular conveyor or depositor of reagents or waste products, respectively. An alternative configuration is a rectangular volume, wherein the third assembly can slide relative to fluid exchange ports on a first assembly which includes a reaction chamber. The third assembly can be constructed of a number of materials including without limitation optical grade glass, silicon-based materials or plastic. In some cases, it may be necessary to surface treat the material, for instance with chloromethylsilane or dichlorodimethylsilane, to minimize the sites on the material that bind to biological molecules such as proteins or nucleic acids. A highly favored material is polyethylene (PE), particularly high density grade PE, which is favorably tolerant of high temperatures. When constructed of plastic, the third assembly is preferably formed by injection molding.

Generally, the cover 130 of a third assembly is formed separately from bottom tray 110. The cover 130 is adhered to the tray 110 by, for instance, pressing these parts together while applying heat until the two materials fuse, and then rapidly cooling while continuing to press the parts together until the fused junction solidifies. The seals between the sidewalls 122 of the chambers 120 and the cover 130 are generally fluid-tight. The cover 130 is formed either of a deformable polymeric material which is stretchable and elastic, or of a more rigid material, such as glass. If a more rigid material is used it preferably has a coefficient of expansion comparable to that of the material forming the tray 110. However, this similarity of thermal expansion is not critical in this context because the carousel is removed from the portions of the assay system that are subjected to cycling between two or more temperatures.

Where the cover 130 is made up of a deformable material, the fluid impeller for impelling fluid to flow from chamber 120 to chamber 250 can be a mechanical plunger with substantially as much cross-sectional area as will allow the plunger to fit within the walls of the chamber 120 to drive the fluid out through the fluid exchange port and into a properly aligned reaction chamber. Where the carousel 100 is rotatable, it can be rotated to position the chamber 120 under such a plunger when the assay (or other reaction) being conducted in the assay system calls for the fluid in the chamber 120 to be transferred into the chamber 250. Similarly, in a rectangular system, the first and third assemblies slide relative to each other to align fluid exchange channels that connect reagent-containing third chambers to reaction chambers. This rotation or sliding is calibrated to align the fluid exchange port in communication with the fluid chamber with either the fluid exchange port in communication with the first or second fluid exchange channel, 231 or 232, respectively, regarding the carousel embodiment) of a reaction chamber. In some embodiments, when the channel 231 or the channel 232 is aligned with a fluid exchange port 121, the other channel (231 or 232) is aligned with another port 121; this dual alignment allows fluid to be inserted into the disk 200 through one port 121, while the gas or fluid previously present in the disk 200 is forced out through the other port 121. In other embodiments, the disk 200 is evacuated prior to the insertion of a fluid, which facilitates the subsequent fluid insertion.

Another means of impelling a fluid to flow from chamber 120 to chamber 250 requires aligning an auxiliary block (such as upper auxiliary block 300A of FIG. 4A) over chamber 120 having a deformable cover. The auxiliary block includes a plurality of gas vents that are used to create a pressure against the cover 130 to deform it downwards to move the fluid out of the fluid chamber. The spacing between the block 300A and the inflexible portion of the cover 130 adhered to the sidewalls 122 of a chamber 120A–120Q are sufficiently narrow to allow enough pressure to be applied to the fluid so that it will move out of the chamber 120 through the port 121. A mechanism of this type is illustrated in FIG. 4A. This type of mechanism can be operated in reverse by applying a vacuum to the vents so that the cover 130 will seek to adhere to the auxiliary block surface. As the auxiliary block, together with the adhered cover 130 is drawn away from the chamber 120, a partial vacuum is created in the chamber, causing fluid to be drawn into the chamber.

In another embodiment, the fluid chambers have valved portals 124 connected to the outer edge of the carousel (see FIG. 3A). The carousel 100 can be operated at a right angle to the orientation illustrated, so that the chamber 120 from which a liquid is to be evacuated can be aligned above the chamber 250. Gas can be admitted through portal 124 to the chamber 120 to force fluid to evacuate the chamber 120 through the exchange port 121 located at the bottom of the chamber 120. One way to assure that gas is not admitted into the chamber 250 is to design the chamber 250 with less volume than the chamber 120, thereby causing the chamber 250 to fill before all the liquid is drained from the chamber 120. A gas with low solubility in aqueous solutions, such as helium, will generally be preferred in this context.

The valve of portal 124 can be a check valve allowing the admission of fluids but blocking outward flows of fluids from chamber 120. Alternatively, the valve can be an electromagnetically actuated valve connected to contacts on the outer surface of the carousel. These contacts can be aligned with other electrical contacts that provide the power to actuate the valve.

FIG. 3 illustrates an alternative embodiment of the bottom tray 110 where the fluid chambers 120A1, 120B1 et seq. comprise a plurality of variously sized chambers of round cross-sectional shape. The cover 130 can be replaced by plungers that are permanently aligned with the chambers 120A1 etc. If the carousel 100 is designed to rotate, the plungers are fixed to a superstructure that rotates with the carousel 100. To increase the disposability of all components that contact assay fluid, the plungers, and even the superstructure, are preferably fabricated out of an inexpensive, easily molded material such as a plastic. In a preferred embodiment, to facilitate the formation of a tight seal, a material "C" is used to construct the plunger and a material "D" is used to construct the walls of the fluid chamber, wherein materials C and D have Rockwell hardness values that are equal to or greater than R50 to insure that the assemblies will not deform in use. Equally important is use of a material with a low permeability to water such as polyethylene. In a preferred embodiment, C is a R50 polyethylene, while D is a R110 polyearbonate.

Alternatively, fluid can be drawn out of or into the chambers 120A1 etc. of FIG. 3 by the same mechanisms described above.

In one embodiment, the carousel 100 has chambers 120 on the top half and additional chambers 120 on a bottom half (not illustrated). In this embodiment, the assay system can have two means for impelling a fluid to leave a chamber 120: one aligned with the upper part of the carousel and the other aligned with the lower half.

Where the assay system is designed to accommodate more than one chamber 250, such as disk 200, there will preferably be at least about nine chambers 120 per first assembly, more preferably at least about fifteen (15) chambers 120 per first assembly, yet more preferably at least about twenty (20) per first assembly.

In addition to the fluid chambers 120, in some embodiments there will be one or more conduits 125 through the third assembly, each conduit having a first opening 126 at the inner ring surface 140 capable of aligning with a first or second fluid exchange channel (231 or 232, respectively). The conduits will have a second opening 127 capable of forming a union with a source of a gas or liquid, such as, without limitation, a wash fluid or an inert gas.

Typically, the exchange ports 121, conduits 125 and portals 124 are channels or openings of diameter between about 125 micrometers ($\mu$m) and about 1250 $\mu$m, preferably about 500 $\mu$m. Typically, the carousel 100 has a diameter between about 8 cm and about 10 cm and a depth between about 5 millimeters (mm) and about 8 mm. Other configurations of the third assembly occupy similar volume, having, for example, a length of between about 7 cm and 9 cm for a square configuration and a depth of between about 5 mm and about 8 mm.

The first assembly comprises one or more reaction chambers and can be constructed of the same materials as those set forth for the third assembly. In one embodiment, the disk 200 is made up of a structural ring 210 with a first and a second exchange channel (231 and 232, respectively), as illustrated in FIGS. 2A and 2B. The ring 210 fits snugly within the inner ring surface 140 of the carousel 100, thus rendering the assay system fluid tight upon assembly.

In one embodiment, the chamber 250 is formed by stretching two thin, deformable membranes 241 and 242 across the structural ring as illustrated in FIGS. 2C and 2D. Preferably, the membranes 241 and 242 are formed of a deformable polymeric film that is stretchable and flexible, such as polyethylene, polyvinylidene fluoride or polyethylene/polyethylene terepthalate bi-layer. Suitable films are available, for instance from Kapak Corporation of Minneapolis, Minn. or E.I. dupont de Nemours and Co., Wilmington, Del. Preferably, the membranes 241 and 242 are resistant to temperatures as high as about 120° C. Preferably, the membranes 241 and 242 are between about 25 and about 150 $\mu$m in thickness, more preferably, between about 50 and 100 $\mu$m. The thinness of the membranes facilitates rapid heat exchange between the reaction chamber and an adjacent heating or cooling device. Preferably, the total volume of each chamber 250 is between about 5 $\mu$l and about 200 $\mu$l, more preferably, between about 20 $\mu$l and about 100 $\mu$l. Preferably, the chamber 250 has a thickness (i.e., distance between covers 251 and 252) of about 1 mm or less.

When the chamber 250 has a deformable upper cover 251 or lower cover 262 (or both), forces can be applied to these covers in the same ways described above for the chambers 120 to push fluids into or out of the reaction chamber. A preferred means of doing this is illustrated in FIGS. 4A, 4B and 4C. Note, however, that while the illustrations show both the upper cover 251 and cover 252 being deformed to move fluid into or out of a reaction chamber, one of these covers can be inflexible and fluid can be moved into or out of such a reaction chamber using only the deformation of the one stretchable cover.

The chamber 250 can be designed so that when a fluid exchange channel 231 or 232 is aligned with the fluid exchange port 121 of a given chamber 120, the other fluid exchange channel is sealed (i.e., not aligned with a fluid exchange port). In this position, fluid can be forced from the chamber 250 into the aligned fluid chamber 120, for instance, using the mechanism illustrated in FIG. 4B. Fluid can then be drawn into the chamber 250 by aligning an exchange channel 231 or 232 with another chamber 120 and forcing the fluid in the chamber 120 into the chamber 250. The fluid can be drawn into the chamber 250 using positive pressure applied via mechanisms associated with the carousel 100, or with negative pressure such as that applied through the mechanism illustrated in FIG. 4C.

To increase the assay variables that can be accommodated on a single assay system, the first assembly, such as a reaction chamber disk 200, preferably includes more than one chamber 250, preferably at least three, more preferably at least five. A disk 200 with three reaction chambers 250A–C is illustrated in FIG. 5. Note that the illustrated disk 200 is designed so that each chamber 250 can interact with its own set of chambers 120, with each such set of chambers 120 situated within a separate 120° arc of the reaction cassette. In a preferred embodiment, the covers 251 or 252 of the chambers 250 of a disk 200 are flexible membranes 241 and 242.

When using a multi-reaction chamber system in conjunction with mechanisms that push fluid into or out of the reaction chambers, some of the mechanisms for doing so that are described above may need modification in ways that will be apparent to those of ordinary skill. However, the task of making these modifications is made easier because typically fluid will be inserted or evacuated from all of the reaction chambers at the same time. Because of this concurrent operation of the reaction chambers, the pressure control mechanism of evacuating or filling reaction chambers that is illustrated in FIGS. 4A–4C should not require modification beyond, perhaps, altering the distribution of the fluid channels 321A and 321B to better align the passageways with the reaction chambers.

When the first assembly contains multiple reaction chambers, such as a reaction chamber disk as illustrated in FIG. 5, the fluid chambers suitable for use with, for instance, the first chamber 250A has a channel 231A at a first position on outer surface 216, while a second chamber 250B has a fluid exchange channel at a second position on outer surface 216. Additional chambers 250 have exchange channels at other distinct positions. Each chamber 120 suitable for use with a given chamber 250 has a port 121 positioned at a position on inner surface 140 appropriate for aligning the port 121 with the channel 231 of the corresponding chamber 250.

Typically, the channels 231 and 232 have a diameter between about 125 $\mu$m and 1250 $\mu$m, preferably about 500 $\mu$m. Typically, the disk 200 has a diameter between about 7.5 cm and about 10 cm, and a depth that approximately corresponds with the depth of the carousel 100; first assemblies used in the context of other configurations of the assay system occupy similar volumes as was analogously discussed above with respect to the third assembly.

Important variables in determining the quality of the seal between the first and third assemblies, such as the surface 140 of the carousel 100 and outer surface 216 of the disk 200, are the smoothness of and the fit between these two surfaces. When using a plastic, one way to achieve a sufficiently smooth surface is to form the surfaces by injection molding. The injection molding methods described by U.S. Precision Lens (Cincinnati, Ohio) or Matrix Inc. (Providence, R.I.) are particularly suitable for dimensional reproducibility of small assemblies.

In a preferred embodiment, to facilitate the formation of a tight seal, a material "E" is used to construct surface 140 and a material "F" to construct the outer surface 216 of the disk 200, wherein materials E and F have Rockwell hardness values as given previously. In a preferred embodiment, E is a R50 polyethylene, while F is a R110 polycarbonate.

The third or the first assembly, such as the carousel 100 or the disk 200, respectively, will generally be attached to a motorized, mechanical means of sliding or rotation. Such sliding or rotational devices are well-known in the engineering arts. Preferably, the means of sliding or rotation is sufficiently precise to reproducibly align the first channel 231 or the second channel 232 with any given fluid exchange port 121 when the controller 400 selects such an alignment as appropriate for a given part of an assay protocol. For instance, the position notch 101 of the carousel embodiment illustrated in FIG. 1A can be used to precisely fit the carousel within an outer ring that has a uniform set of gear teeth on its outer edge. The gears, in turn, interact with a stepper motor operating under the direction of the controller 400.

Typically, when one of the disks 200 or the carousel 100 is attached to a motorized means of rotation, the other will be fixed in place during the operation of the assay system. This locking into place reduces the alignment variables and improves the reproducibility of alignment between the carousel 100 and the disk 200.

Numerous means of rotating or sliding one of the third or first assembly, e.g., the carousel or the reaction chamber disk, will be apparent to those of ordinary skill in the mechanical arts.

The upper or lower second assembly 300A or 300B (or, of course upper and lower second assemblies 500A or 500A) can contain a plurality of upper or lower pressurized fluid channels 321A or 321B. The fluid within these channels is typically a gas. Gas of higher than atmospheric pressure can be applied to the channels 321A or 321B from, for instance, a pressurized gas canister or a pump applied to upper or lower gas inlet/outlets 310A or 310B. A vacuum, usually a partial vacuum, can be applied to the channels 321A or 321B using, for instance, a vacuum pump. Numerous mechanisms for controlling the pressure of the pressurized fluid channels will be recognized by those of ordinary skill in the engineering arts.

As part of a mechanism for creating a vacuum in an adjacent reaction chamber 250, the block 300A or 300B can have a means for drawing the block 300A or 300B away from the chamber 250, thereby drawing an adherent, stretchable cover 251 or 252 away from the reaction chamber. Such means of drawing the auxiliary block away will typically be a mechanical or electromechanical device. Such devices are well-known to those of ordinary skill in the engineering arts.

In a preferred embodiment, either, (1) at least one reaction chamber has a transparent external wall that is generally an upper cover or lower cover (or two external walls are transparent), such as in structures 250, 251 and 252 in FIG. 2B, or (2) at least one fluid chamber has a transparent external wall that is generally the top cover or bottom of the chamber (or two external walls are transparent). The assay system in this embodiment preferably includes a light source capable of directing light to the transparent cover or bottom and a detection device for detecting (a) the light reflected from an illuminated chamber (such as 250 or 120 in FIG. 8A or 8B, for example), (b) the light transmitted through an illuminated chamber (250 or 120), or (c) the light emissions emanating from an excited molecule in a chamber (250 or 120). An external wall is "transparent" if it is at least about 80% transparent at a wavelength useful for detecting biological molecules.

The detection device can incorporate optical fibers. With fiber optics, the size of the detection system that is adjacent to the assay system is minimized. This size minimization facilitates incorporating the detection system together with the temperature control device (incorporated in the second assembly) and rotational mechanism into the assay system. A particularly preferred light source is a solid state laser. The size of these light sources also facilitates incorporating a number of auxiliary assemblies about the assay cassette. When PCR is conducted in an assay system that incorporates current technology solid state lasers, the method used to detect amplified nucleic acid uses a dye that absorbs light at a wavelength higher than about 600 manometers (nm) to indicate the presence of amplified nucleic acid, as described below. Examples of such dyes include $Cy_5$™ conjugated reagents (Jackson ImmunoResearch Labs, Inc., West Grove, Pa.), which reagents absorb in the 600–650 nm range and emit a fluorescent signal in the 630–750 nm range, allophycocyanin and allophycocyanin-conjugated reagents (Sigma Chemical Co., St. Louis, Mo.), and C-phycocyanin and C-phycocyanin-conjugated reagents (Sigma Chemical Co., St. Louis, Mo.). The relatively high wavelengths described above avoid much of the background fluorescence associated with oligonucleotides, plastics and other components of the assay system. A preferred solid state laser source is a Laser Max, Inc. (Rochester, N.Y.) Model LAS-200-635.5.

Signals from the detection device will typically be input into the controller 400, where they can be used to determine whether an assay should continue or to generate an assay report.

The speed with which the temperature of the chamber 250 is increased or decreased is important for optimizing various enzymatic-based assays, including PCR-based assays. During the temperature cycling important for PCR, it is important to operate at a relatively lower temperature where the nucleic acid sample is enzymatically reproduced and at a higher temperature where the nucleic acid sample is melted to separate the two strands of the nucleic acid. During the period when the assay apparatus cycles between the two preselected temperatures believed to be appropriate for a given nucleic acid amplification, various unwanted chemistries can be expected to occur. For instance, as the temperature increases from the lower temperature, the replication enzyme can be expected to continue to function, although not necessarily with the appropriate accuracy of replication achieved at the prescribed lower temperature. At the higher temperature set point, this unwanted enzymic activity is inhibited by the high temperature. Thus, it is important to rapidly change the reaction temperature between the two operating temperature plateaus.

One mechanism by which the temperature can rapidly be changed in the reaction chamber is illustrated in FIGS. 6A and 6B. Although this illustration is provided with respect to a circularly-configured assay system, the same heat source and cooling sink elements can be used in the context of the assay system of any suitable configuration, as would be understood by those skilled in the art. Assume that the chamber 250 is operating at lower plateau temperature "G". Under these conditions, cooling water does not flow through upper and lower conduits 330A or 330B. The temperature is maintained by intermittently operating upper and lower heaters 340A and 340B when the temperature in the chamber 250 lowers beneath a temperature of G minus X (where X is a temperature differential). At a pre-programmed time, the temperature is raised to higher plateau temperature "H" by activating heaters 340A and 340B until a temperature is reached that will lead to a temperature stabilization at temperature H. Water flow through conduits 330A and 330B can be activated to minimize temperature overshoots if needed, which action tends to increase the cooling sink efficiency of the second assembly. Temperature H is maintained by intermittently operating heaters 340A and 340B when the temperature of the chamber 250 lowers beneath a temperature of H minus Y (where Y is a temperature differential). To cycle back to temperature G, the controller activates the pump 351 (not illustrated) of console 350 to cause cooling water to flow through conduits 330A and 330B of the second assembly. In another embodiment, the cooling sink effect is provided by a suitable material of adequate heat exchange capacity and sufficient mass thereof that is reversibly brought into contact with the reaction chamber in need of being cooled.

The heaters 340A and 340B are generally thin layers of conductive material that is separated from the heat conductive upper and lower section 302A and 302B of blocks 300A and 300B by a thin electrical insulation layer. The blocks are referred to herein as second assemblies of the assay system, which assemblies comprise a heat source and a cooling sink. Alternatively, or in addition, such second assemblies can comprise a mechanism for pushing or pulling a deformable cover on a fluid or reaction chamber. The insulation layer is formed, for example, by direct deposition onto the substrate. For example, silicon nitride can be deposited from the gas phase or aluminum oxide can be deposited using a liquid carrier. The conducting layer forming heaters 340A and 340B are, for example, deposited by vacuum evaporation (e.g., for a nichrome conducting layer) or by deposition from the vapor (e.g., for an indium tin oxide conducting layer). Alternately, pre-formed heater sheets are cemented to the substrate, for instance using an epoxy cement or the adhesive recommended by the vendors. Appropriate heaters can be obtained from Elmwood Sensors Inc. (Pawtucket, R.I.) or from Omega Engineering Inc. (Stamford, Conn.).

In some embodiments, the thermal contact between the heaters 340A and 340B and the blocks 300A and 300B, respectively, will be sufficient so that the temperature of block 300A or 300B can be expected to closely approximate the temperature of the adjacent chamber 250. Accordingly, temperature monitoring means can be mounted to the block 300A or 300B. In other embodiments, typically those where pre-fabricated heaters are mounted onto the auxiliary blocks, other methods of measuring reaction chamber temperature may be required. One such method is illustrated in FIG. 6C, which shows an upper extension 303A on the outer face of the block 300A. The extension 303A is generally fabricated of the same material as upper section 302A. Upper second thermal sensor 306A provides more direct evidence of the temperature in chamber 250, while upper first thermal sensor 304A provides diagnostic temperature information.

To maximize the thermal transfer between the heaters and the chamber 250, the covers 251 and 252 of the chamber 250 are preferably constructed of a flexible material that can conform to the surface of the heater 340A or 340B placed against such a flexible cover.

The non-conductive upper and lower portions 301A and 301B of blocks 300A and 300B are fabricated from a nonconductive material such as, without limitation, nylon or polycarbonate. The conductive upper and lower sections 302A and 302B of blocks 300A and 300B are fabricated from a material such as, without limitation, aluminum or copper.

FIG. 7A shows alternate heater and cooling devices within upper and lower auxiliary blocks 500A and 500B. The illustrated blocks 500A and 500B function to narrow or expand the chamber 250 just as do the blocks 300A and 300B of FIGS. 4A–4C. The elements such as 511A and 512B are made of a suitable material to provide a strong thermoelectric effect at their junction. Heating is achieved by applying voltage of the proper polarity to upper first and second leads 508A and 509A and to lower leads 508B and 509B. Cooling is achieved by reversing the polarity of the voltage. An important variable in the operation of these heating and cooling devices is temperature uniformity. To increase temperature uniformity, upper and lower first endplates 502A and 502B are preferably constructed of a material of high thermal conductivity, such as sintered beryllia. Other suitable materials include, without limitation, ceramics containing aluminum. Preferably, the thermal conductivity of end-plates 502A and 502B is at least about 0.2 watt/cm$^{-1}$/K$^{-1}$, more preferably at least about 2 watt/cm$^{-1}$/K$^{-1}$. The upper and lower temperature sensors 570A and 570B can be, without limitation, thermocouples or resistive sensors. The sensors 570A and 570B can, for example, be deposited on the end-plates 502A and 502B as thin films or they can be in the form of thin wires embedded into holes in the end-plates 502A and 502B.

Using these heating and cooling devices, including the device described in the immediately preceding paragraph, chamber 250 temperatures between about −20° C. and about 100° C. can be maintained. The higher temperature may require a subsidiary heater to give a constant temperature bias to the blocks 504A and 504B. The temperature in a reaction chamber preferably can jump from about 25° C. to about 75° C. in about 10 seconds, more preferably in about 5 seconds, and more preferably yet in about 3 seconds. The reciprocal cooling step is preferably achieved in about 10 seconds, more preferably in about 5 seconds, and more preferably yet, in about 3 seconds. Preferably, after a cooling or heating step, the variation in temperature in the reaction chamber is no more than about 1° C., more preferably no more than about 0.5° C., yet more preferably, no more than about 0.1° C.

In one preferred embodiment, when the disk 200 includes more than one reaction chamber 250, each such chamber 250 will have at least one heating and cooling device made up of thermoelectric blocks 501 (such as the heating and cooling device described in the paragraph immediately above) capable of being aligned with a side of the reaction chamber. More preferably, each chamber 250 will have a heating and cooling device on each of two opposing sides. In another preferred embodiment, the cross sectional area of the end-plate 502A or 502B substantially matches the largest cross-sectional area of the chamber 250 to which it is intended to transfer heat.

The principles of temperature cycling for chambers 250 heated and cooled with blocks 500A and 500B are the same as those outlined above for the blocks 300A and 300B of FIGS. 6A, 6B and 6C.

In another embodiment, the reaction chamber is heated and cooled by passing a heated or cooled fluid, preferably a gas, either directly over one or more surfaces of the chamber 250 or through a heat exchange apparatus that can be positioned adjacent to one or more surfaces of the reaction chamber. The apparatus illustrated in FIGS. 6A and 6B can be modified to operate pursuant to this embodiment by (a) removing (or not using) the heaters 340A and 340B and (b) adding a heater for heating the fluid. The system preferably has two fluid management systems, one for a hotter fluid and another for a cooler fluid, together with the valuing required to inject the hotter or cooler fluid into the tubing leading to the chamber 250 as appropriate for maintaining a given temperature in the reaction chamber. Particularly where the heating and cooling fluid is a gas, the temperature of the gas soon after it has passed by the reaction chamber will provide a useful indication of the temperature of the reaction chamber.

The uniformity of the reactions conducted in the chambers 250 can be increased with paramagnetic beads agitated by a rotating magnetic field. Such paramagnetic beads are available from several sources including Bang Laboratories (Carmel, Ind.) for beads lacking conjugated biomolecules, Dynal (Lake Success, N.Y.) for beads conjugated to various antibodies (for instance, antibodies that bind to the CD2 cell-surface receptor) and CPG (Lincoln Park, N.J.) for beads with a glass matrix and a variety of surface bonded organics. For applications where it is anticipated that the beads will be washed into and out of reaction chambers, each bead will preferably have a diameter of less than about 25 $\mu$m, more preferably, less than about 12.5 $\mu$m, which diameter facilitates entry and exit through the channels by which material is inserted or evacuated from the chamber 250. For applications where the beads are anticipated to remain in the chamber 250, in one embodiment, the diameter is preferably sufficiently large to preclude their entry into these channels. The entrances to such channels within the chamber 250 are preferably positioned or designed so as to minimize the chance that a channel will be blocked by a bead that settles over the channel's entryway. In another embodiment, the beads are locked in place using magnetic fields.

To generate sufficient movement among the beads, it has been determined that the magnet used should preferably generate a sufficient magnetic field gradient within the chamber 250. Such magnets can be constructed by forming sharp edges on highly magnetic permanent magnets, such as those formed of rare earths, such as the neodymium-iron-boron class of permanent magnets. Such a permanent magnet is available from, for example, Edmund Scientific (Barrington, N.J.). Sharp edges of dimensions suitable for a particular reaction chamber are, for example, formed by abrasive grinding of the magnetic material. An example of such a shaped magnet 600 is shown in FIG. 10, where the N pole of the magnet has a roof-shape. To maximize the field gradient acting on the paramagnetic beads, the peak 601 of the magnet 600 is placed adjacent to the reaction chamber or other structure in which the beads are located. The beads are stirred by rotating the magnet 600 about its N to S axis. The paramagnetic beads are held in place by leaving the peak 601 adjacent to the beads. By sliding the magnet with its peak 601 adjacent to the beads, the beads are impelled to move with the magnet.

The sharp-edged magnets described above are effective in adhering the paramagnetic beads in one place and in moving beads located, for instance, in a capillary or in a reaction chamber, from one location to another. Such magnets thus can help retain the paramagnetic beads in one place, for instance when a fluid in the chamber 250 or a chamber 120 is being removed from that chamber but it is desirable to leave the beads in the chamber.

Various cell binding beads (e.g., beads having bound antibodies specific for a certain subset of cells) can be used to adhere selected cells from a population of cells. The beads can be locked in place, for instance magnetically if the beads are paramagnetic, while non-adherent cells and fluids are washed away. Thus, cell-binding beads can be used to concentrate small sub-populations of cells.

In the PCR reaction, mixing can be important in the preparatory steps prior to the amplification reaction. However, during the subsequent temperature cycling, mechanical mixing can be omitted. Thus, in some embodiments, the rotatable magnet that induces the mixing movement of the beads can be placed adjacent to the chamber 250 immediately after the various reagents are introduced. The reagents can then be mixed, and the magnet withdrawn to facilitate the placement of other mechanisms, such as heating and cooling devices, adjacent to the chamber 250.

The controller 400 will typically be a microprocessor. However, it can also be a simpler device comprised of timers, switches, solenoids and the like. The important feature of controller 400 is that it directs the movement of the carousel 100 or disk 200, the activation of the means for impelling a fluid, and the heating and cooling device according to a pre-set or programmable schedule that results in the operation of an assay protocol, such as one of the protocols outlined below. Preferably, the controller receives input indicating the temperature of the reaction chambers of the assay cassette and is capable of adjusting its control signals in response to this input.

Often an important variable in PCR reactions is the amount of interfering cellular debris, including cellular chemicals, present in the sample to be assayed. Ideally, only highly purified nucleic acid is used as the sample subjected to a PCR amplification. However, such purification is not practical with the small amounts of tissue or fluid available for a diagnostic assay. Further, given the sensitivity of the assay to contamination by environmental sources of nucleic acid, a nucleic acid purification step can increase the likelihood of getting a false positive result. In some areas of diagnostic or forensic PCR this concern about interference by cellular debris has been eased somewhat by improvements in the characterization of PCR reaction conditions, such that often much cruder nucleic acid samples can be used without adverse effect. See Rolfs et al., *PCR: Clinical Diagnostics and Research*, Springer Lab, 1992 (particularly Chapter 4 et seq.). See, also, the literature available with such commercial products as GeneReleaser™ (BioVentures, Inc., Murphreesboro, Tenn.), Pall Leukosorb™ media (Pall, East Hills, N.Y.) and Dynbeads™ DNA Direct™ (Dynal, Lake Success, N.Y.). On PCR procedures, see generally, Ausubel et al., *Current Protocols in Molecular Biology*, John Wiley & Sons, New York (AUSUBEL I) and *PCR: A Practical Approach*, IRL Press, 1991 (AUSUBEL II). Nonetheless, it is desirable to have the capability of at least removing the cellular debris associated with the cell membranes of the cells that may be present in the sample. Such a technique for use in conjunction with the assay system is described below. Such a cleanup step can be applied when needed to achieve the needed level of sensitivity or accuracy, or omitted if not needed.

It is also important to conduct parallel control PCR reactions when conducting PCR. One important type of control omits sample from the reaction or uses a sample previously characterized as negative. Another important type of control introduces a known amount of a purified nucleic acid that is known to contain the sequence or sequences that the PCR reaction is designed to amplify. These types of controls can be accomplished on multiple assay system units or cassettes, or, more preferably, in separate reaction chambers on the same first assembly, such as the disk 200.

Another control technique used in PCR is to design the PCR reaction so that it will amplify multiple nucleic acid segments, each indicative of a disease or a genetic circumstance. The different segments can be amplified in multiple reactions or in the same reaction chamber. If amplified in the same chamber, experience in the field has indicated that binding competition between the various primers necessitates extending the time, in each amplification cycle, spent at the replication temperature.

One tool for removing cellular debris from a sample involves first binding the cells in the sample to a bead that has attached thereto an antibody specific for a cell surface molecule found on the cells. Beads that bind to the CD2 molecule found on white blood cells or to *E.coli* bacteria (such as the 0157E strain) are available from Dynal (Lake Success, N.Y.). An ever-growing family of cell-surface molecules found on mammalian cells, bacterial cells, viruses and parasites has been characterized and antibodies against the majority of these molecules have been developed. See, e.g., *Adhesion Molecules*, C. D. Wegner, ed., Academic Press, New York, 1994. Many of these antibodies are available for use in fabricating other types of cell-affinity beads (for instance, from Sigma Chemical Co., St. Louis, Mo.). The cells can be adhered to the beads and lysed to release their nucleic acid content. The lysis fluid together with the released nucleic acid can be moved to a separate compartment for further processing, leaving behind the beads and their adherent cellular debris.

The lysis fluid used to release nucleic acid from the sample cells can also interfere with the PCR reaction. Thus, in some protocols it is important to bind the nucleic acid to a substrate so that the lysis fluid can be washed away. One such support is provided by beads that bind to DNA, such as glass beads that bind to DNA by ionic and other interaction forces. Suitable beads, with surfaces chemically treated to maxmiize the number of interaction sites, are available from, for example, BioRad (Hercules, Calif.). Paramagnetic beads with a number of DNA binding surfaces, such as nitrocellulose or nylon-coated surfaces are anticipated to be useful in operating the invention. In some embodiments, it is desirable for the beads to be paramagnetic so that they can be manipulated using magnetic forces. Paramagnetic glass beads are manufactured by Dynal (Lake Success, N.Y.) or CPG (Lincoln Park, N.J.). Once the nucleic acid is bound to the beads, the lysis fluid can be washed from the beads. The nucleic acid can be amplified with the beads present.

The lysis fluid used to release nucleic acid from the cells in a sample typically includes a detergent, preferably nonionic, and a buffer, usually the buffer used in the PCR amplification reaction. The pH of the lysis fluid is preferably about pH 8 to about pH 8.5. Suitable detergents include, without limitation N-lauroylsarcosine, sold under the tradename Sarkosyl (Sigma Chemical Company, St. Louis, Mo.), and octylphenoxy polyethoxy ethanol, sold under the tradename Nonidet P-40 (also Sigma Chemical Company). Other assemblies can include salts, including $MgCl_2$, chelators and proteases such as proteinase K Proteinase K can be inactivated by heating, for instance, to about 100° C. for about 10 minutes. Depending on the composition of the lysis buffer, it can be more or less important to wash the lysis buffer away from the nucleic acid prior to conducting the amplification assay.

The amplification buffer used to support the amplification reaction will typically include the four deoxynucleotide triphosphates (NTPs) (e.g., at a concentration of from about 0.2 mM each), a buffer (e.g., Tris-HCl, 10 mM), potassium chloride (e.g., 50 mM) and magnesium chloride (e.g., 1 to 10 mM, usually optimized for a given PCR assay scheme). The pH is typically about pH 8.4. Other components, such as gelatin (e.g., 0.1 mg/ml), can be added. The individual primers are typically present in the reaction at a concentration of about 0.5 $\mu$M. The amount of sample nucleic acid needed varies with the type of nucleic acid and the number of target nucleic acid segments in the nucleic acid sample. For genomic DNA, where each cell in the sample has about 2 copies of target nucleic acid, a concentration of about 10 $\mu$g/ml is desirable.

For simplicity, the polymerase used in the procedure is a heat-resistant DNA polymerase such as Taq polymerase, recombinant Taq polymerase, Tfl DNA polymerase and Tli DNA polymerase (all from Promega Corp., Madison, Wis.). Heat stability allows the PCR reaction to proceed from cycle to cycle without the need for adding additional polymerase during the course of the reaction process to replace polymerase that is irreversibly denatured when the reaction vessel is brought to a DNA strand separation temperature. Preferably, the DNA polymerase used has the increased accuracy associated with the presence of a proofreading, 3' to 5' exonuclease activity, such as the proofreading activity of the Tli DNA polymerase.

Blood provides one of the more convenient samples for diagnostic or genetic PCR testing. For most genetic testing, from about 10 to about 50 $\mu$l of blood is sufficient to provide enough sample DNA to allow for PCR amplification of specific target segments. For fetal cell analysis, however, as much as about 20 mls, which may contain as few as about 400 fetal cells, can be required. Such large sample volumes require concentration, for instance, using the methods described above. For testing for microbial diseases, the concentration of target nucleic acid in the sample can be quite low (e.g., no more than about 2 fg to about 5 fg per bacterial genome). Thus, when using the assay system to test for such microbes, concentration methods may again be required.

To specifically amplify RNA, it is necessary to first synthesize cDNA strands from the RNA in the sample using a reverse transcriptase (such as AMV reverse transcriptase available from Promega Corp., Madison, Wis.). Methods for conducting a PCR reaction from an RNA sample are described, for example, in AUSUBEL I and AUSUBEL II. To prepare RNA for this purpose, a facile procedure uses a lysis buffer containing detergent (such as 0.5% Nonidet P-40), buffer (e.g., pH 8.3) and suitable salts that has been, immediately prior to use, mixed 1:1000 with a 1:10 diethylpyrocarbonate solution in ethanol. After sample cells have been lysed with this solution, a supernate containing RNA is separated away from a pellet of nuclei by centrifugation. Primer, which is generally the same as one of the primers used in the subsequent PCR cycling reaction, is annealed to the RNA by heating, e.g. to 65° C. and subsequently reducing the temperature to, generally, about 37° C. The reverse transcriptase, nucleotide triphosphates and suitable buffer (if not already present) are then added to initiate cDNA synthesis. Generally, a small volume of cDNA synthesis solution is added to a solution containing the buffer, DNA polymerase, nucleotide triphosphates and primers needed for the PCR amplification. The temperature cycling program is then initiated.

These advantages also substantially apply to conducting hybridization procedures. The ability of the valves of the assay system to accommodate elevated temperatures allows the system to be used in hybridization protocols. While hybridization reactions are not as sensitive to contamination as PCR reactions, these reactions are nonetheless very sensitive to contamination, the risk of which is substantially reduced with the disposable system.

Procedures for conducting hybridizations are well known in the art. See, for example, AUSUBEL I and Sambrook et al., *Molecular Cloning: A Laboratory Manual*, 2nd ed., Cold Spring Harbor Press, 1989. In these procedures, one of (a) a sample source of nucleic acid containing a target sequence or (b) a probe nucleic acid is bound to solid support and, after this binding, the remaining binding sites on the support are inactivated. Then, the other species of nucleic acid, which has bound to it a detectable reporter molecule, is added under appropriate hybridization conditions. After washing, the amount of reporter molecule bound to (i.e. hybridized with) the nucleic acid on the solid support is measured.

For instance, a hybridization can be conducted in a reaction chamber in the assay system, where the reaction chamber contains a piece of nitrocellulose membrane (or another membrane that binds nucleic acid) to which RNA has been bound (for instance, by electrophoretic or capillary blotting from a separation gel, followed by baking). A Northern prehybridization solution can then be introduced into the reaction chamber from one of the fluid chambers. (The recipes for Northern prehybridization solution (p. A1–40), Northern hybridization solution (p. A1–39), SSC (p. A1–53, 20X recipe) and Denhart's solution (p. A1–14, 100X recipe) of AUSUBEL I are incorporated herein by reference to more fully exemplify the hybridization methods that can be conducted in the assay system; note that the salmon sperm DNA recited in two of these recipes, which DNA serves as a competitor to reduce nonspecific hybridizations, is typically sheared prior to use.) The membrane and prehybridization solution are incubated overnight at a temperature between about 37° C. and about 42° C., depending on the melting temperature for the interaction between target sequence and the probe sequence. Note that these incubation temperatures are in the range that is generally appropriate given the presence of 50% formamide in the prehybridization and hybridization solutions; for hybridizations conducted without formamide, incubation temperatures are typically higher, such as about 55° C. or about 70° C. The membrane is then exposed to Northern hybridization solution containing melted probe and incubated overnight at the same temperature used in the prehybridization. Following hybridization, the hybridization solution is pushed out of the reaction chamber, the reaction chamber is brought to about 25° C. and a first wash solution (1X SSC, 0.1% w/v sodium dodecyl sulfate) is introduced. After 15 minutes, the wash is repeated. After an additional 15 minute wash, a third and final wash is conducted using 0.25X SSC, 0.1% W/V sodium dodecyl sulfate.

This hybridization method is exemplary only. Numerous other hybridization methods can be conducted in the assay system, including those described in the following sections AUSUBEL I which are incorporated herein by reference: Unit 2.9, pp. 2–24 to 2–30 and the recipes of Appendix 1 referred to therein; Unit 6.3, pp. 6–6 to 6–7 and the recipes of Appendix 1 referred to therein; and Unit 13.12, p. 13–44 and the recipes of Appendix 1 referred to therein.

The elevated temperatures required for hybridization reactions can be handled in an automated apparatus. For instance, hybridizations can be conducted at a temperatures approximately defined by the melting temperature ($T_m$). $T_m$ values for any hybridization probe can be calculated using commercially available software such as Oligo™ v4.0 from National Biosciences, Inc. Plymouth, Minn.

In immunoassay procedures, which are conventionally known to the art, the antibody-antigen binding reactions are generally conducted at room temperature or at a reduced temperature, such as about 4° C. After the binding reactions, positive results are generally indicated by an enzymic reaction, such as that mediated by the enzyme alkaline phosphatase, which enzyme reaction is generally conducted at a temperature between about 20° C. and about 40° C. The assay allows these assays to be automated in a system that allows fast and reliable temperature regulation in the temperature range between about 0° C. and about 40° C.

Typically, modern antibody-based screening procedures use a solid support to which an "antigen" (which is simply a substance that when injected in a suitable form into a suitable animal causes the animal to manufacture antibodies specific for the antigen) or an antibody has been attached. Alternatively, the antigen is found on the surface of a cell, such as a bacteria or eukaryotic cell, and the cell substitutes for a solid support.

In one assay (indirect ELISA), the antigen is bound to the support and a sample prospectively containing a first antibody specific for the antigen and produced by a first animal species is incubated with the bound antigen. After appropriate washing steps, a second antibody from a second animal species, which antibody is specific for antibodies of the first species and is attached to a detectable moiety (such as alkaline phosphatase), is incubated with the support. If the sample contained the first antibody, the second antibody will bind and be detectable using the detectable moiety. For instance, if the detectable moiety is alkaline phosphatase, detection can be conducted by adding a chemical, p-nitrophenyl phosphate, that is converted into a blue substance by the action of the phosphatase enzyme. This assay can, for instance, be used to test blood for the presence of antibodies to the AIDS virus.

In another assay (direct competitive ELISA) that uses a support with bound antigen, a sample that prospectively contains antigen is incubated with the support together with a limiting amount of an antibody specific for the antigen, which antibody has an attached detectable moiety. Due to competition between the solution phase antigen and the supportbound antigen, the more antigen in the sample, the less antibody that is bound to the support-bound antigen and the weaker the signal produced by the detectable moiety.

Another assay (antibody-sandwich ELISA) uses a first antibody specific for an antigen, which antibody is bound to the support. A sample that prospectively contains the antigen is then incubated with the support. Following this, a second antibody that binds to a second part of the antigen, and which has an attached detectable moiety, is incubated with the support. If the sample contained the antigen, the antigen will bind to the support and then bind to the detectable second antibody. This is the basis for a home pregnancy test, where the antigen is the pregnancy-associated hormone chorionic gonadotropin.

In another assay (double antibody-sandwich ELISA) that uses a support with bound antibody, a sample that prospectively contains a first antibody from a first species is incubated with a support that has bound to it a second antibody from a second species that is specific for antibodies of the first species. The antigen for the first antibody is then incubated with the support. Finally, a third antibody specific for a portion of the antigen not bound by the first antibody is incubated with the support. The third antibody has an attached detectable moiety. If the sample contained the first antibody, the detectable third antibody will bind to the support.

These and other immunoassays are described in Units 11.1 and 11.2 of AUSUBEL I pp. 11–1 to 11–17, which text and the recipes of Appendix 1 cited therein, are incorporated herein by reference.

The following examples further illustrate the invention but, of course, should not be construed as in any way limiting its scope.

EXAMPLE 1
Heat Source/Cooling Sink Operation

The performance of a heater device and cooling device used with respect to the illustrated circular configuration of the assay system, and depicted in FIG. 6A, has been simulated using a heat transfer simulation computer program using a finite element approximation to the heat flow equation. The simulation was conducted with the following assumptions: the thickness of the chamber 250 was 0.5 mm, the upper and lower covers were 0.1 mm thick and the insulation between the heater and the auxiliary block was 0.025 mm thick. The simulation determined that with appropriate commercially available materials, a jump from 25° C. to 75° C. can be achieved within 3.2 seconds, where, after 3.2 seconds, the temperature in the reaction chamber is substantially uniform. The reciprocal cooling step can be achieved within about 3 seconds, resulting in a substantially uniform temperature in the reaction chamber.

EXAMPLE 2
PCR Reaction

Figure 8A:
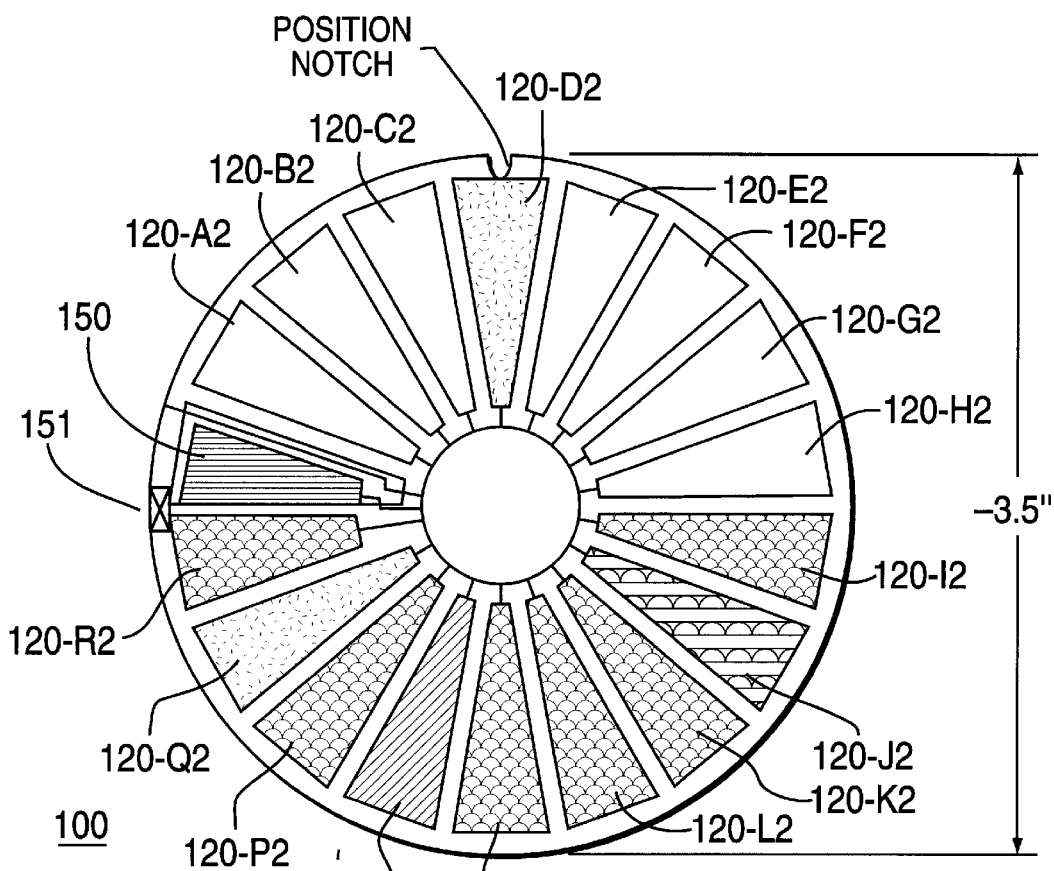
FIGS. 8A and 8B display an assay cassette used in Example 1.
Figure 8B:
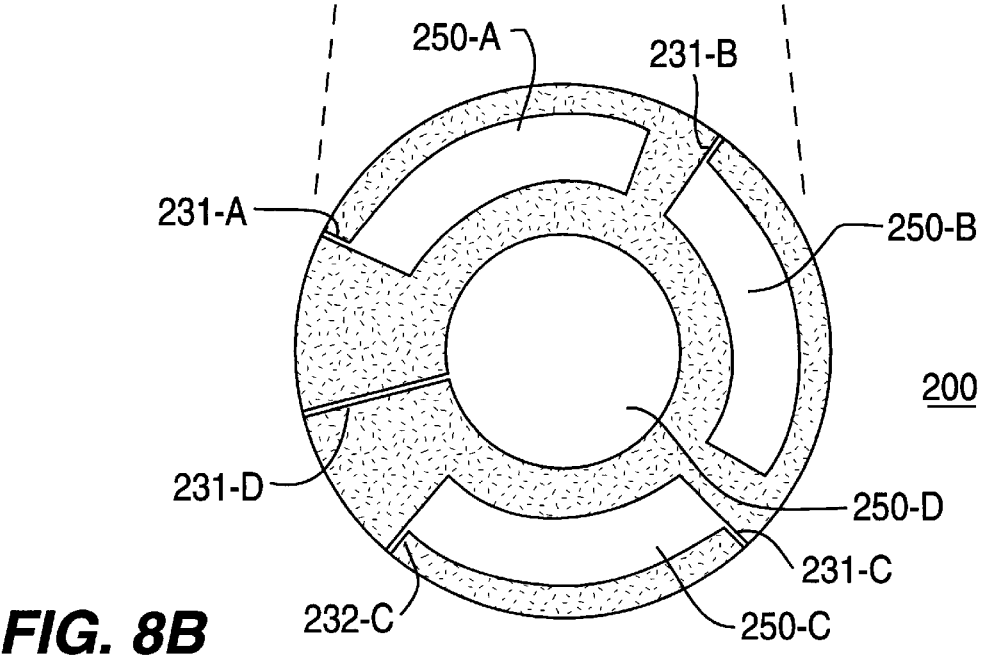

A PCR assay is conducted using the reaction cassette illustrated in FIGS. 8A and 8B, where the reaction chamber disk has first through third reaction chambers 250A–250C of equal volume and a fourth reaction chamber 250D of volume 8% greater than the combined volume of the first and third reaction chambers (250A and 250C). The carousel has seventeen fluid chambers 120A2 through 120R2. The reaction cassette has a capillary tubing structure 150 used to introduce sample into the chamber 250D. The capillary tubing structure has an inlet 151 through which sample is introduced into the capillary system. The assay system has upper and lower auxiliary blocks, the lower of which can be drawn sufficiently away from the reaction chamber disk to allow a rotatable magnet to be positioned under the reaction chamber disk. The assay system has a first fluid impeller for impelling a fluid to move from a fluid chamber (120A2 to 120R2) to a reaction chamber (250A to 250D) and a second fluid impeller for emptying the reaction chambers 250A–250D, both such impellers found in the upper auxiliary block. Steps 1 through 12, outlined below, are conducted with the lower auxiliary block drawn away from the reaction chamber disk and with a rotatable magnet positioned under the disk. The reaction protocol is as follows:

1. Capillary tubing structure 150 is aligned with chamber 250D of the assay cassette and a blood sample in the capillary tubing 150 is drawn into the chamber 250D using air pressure. (The capillary tubing is filled with blood by aligning the outlet of the capillary tubing structure with a vent (not shown) located adjacent to fluid exchange channel 231D on the reaction chamber disk, and filling the capillary structure by capillary action through inlet 151.) The chamber 250D is pre-loaded with a supply of paramagnetic, white blood cell-binding beads having a diameter of 50–100 μm (Dynal, Lake Success, N.Y.). The chamber 250D is maintained at a temperature of 2–4° C. The magnet is rotated to agitate the beads, thereby providing stirring.

2. After 45 minutes co-incubation of the beads and the blood, the carousel of the cassette is rotated until a first fluid chamber 120A2 is aligned with a fluid exchange channel 231D. The excess fluid from the sample, along with unbound cells are pushed into the chamber 120A2. The beads are magnetically restrained from leaving the chamber 250D.

3. At this point, the carousel is rotated to align the chamber 250D with a second fluid chamber 120B2 containing a washing solution composed of amplification buffer (40 mM NaCl, 20 mM Tris-HCl, pH 8.3, 5 mM MgSO$_4$). The washing solution is drawn into the chamber 250D.

4. The carousel is rotated to align the chamber 250D with the chamber 120A2, into which the wash solution is pushed, again leaving the beads magnetically restrained in the chamber 250D.

5. The carousel is rotated to align chamber 250D with a third fluid chamber 120C2, from which a lysis solution (amplification buffer supplemented with 0.5% v/w polyoxyethylenesorbitan monolaurate, sold under the tradename Tween 20 (Sigma Chemical Company, St. Louis, Mo.), and 100 μg/ml proteinase K) is drawn. To lock the lysis solution in place, the carousel is rotated to close the fluid exchange channel 231D. The temperature of the fourth 250D is now maintained at 56° C. Stirring is achieved by rotating the adjacent magnet to agitate the cell-binding beads.

6. After 45 minutes, the carousel is rotated to align the chamber 250D with a fourth fluid chamber 120D2, into which the lysis solution, which contains nucleic acid extracted from the cells of the sample, is pushed. Again, the cell-binding beads remain in the chamber 250D. The volume of lysis solution is 8% greater than the combined volume of the first and third reaction chambers 250A and 250C (exclusive of the volume occupied by nucleic acid-binding beads).

7. The chambers 250A and 250C are pre-loaded with paramagnetic, nucleic acid-binding beads and are evacuated of fluid. The carousel is serially rotated to align the fourth fluid chamber 120D2 with a fluid exchange channel 231A and then with fluid exchange channel 232C, and chambers 250A and 250C are filled with the nucleic acid-containing lysis solution from the fourth fluid chamber 120D2. The beads in the chamber 250C are pre-loaded with a purified DNA the includes the amplification sequence in an amount sufficient to generate a positive result. The chamber 250A is for the experimental amplification. The chamber 250C provides the positive control. The chamber 250B contains only the nucleic acid-binding beads and a pre-loaded volume of lysis solution; it serves as the negative control.

8. The carousel is now rotated to close the chambers 250A–250C. The chambers 250A–250C are maintained at a temperature consistent with the binding material on the beads. For example, for Dynal Dynabeads M-450 Pan T (CDL) binding beads the optimum temperature is 2–4° C.

9. After 15 minutes, which is sufficient time to allow the DNA in the lysis solution to bind the DNA-binding beads, the carousel is rotated to align the chambers 250A–250C with the fifth (120E2), tenth (120J2) and fifteenth (120P2) fluid chambers, respectively, and the lysis buffer is pushed out of the chambers 250A–250C. DNA-binding beads are magnetically restrained from exiting.

10. The carousel is rotated to align the chambers 250A–250C with the sixth (120F2), eleventh (120K2) and sixteenth (120Q2) fluid chambers, respectively, and wash solution (described above) is introduced into the chambers 250A–250C. The DNA-binding beads are agitated magnetically.

11. After 10 minutes, the carousel is rotated to align the chambers 250A–250C with the fifth (120E2), tenth (120J2) and fifteenth (120P2) fluid chambers, respectively, and the wash solution is pushed out of the reaction chambers.

12. The carousel is rotated to align the chambers 250A–250C with the seventh (120G2), twelfth (120L2) and seventeenth (120R2) fluid chambers, respectively, from which is drawn an amplification solution containing amplification buffer (supplemented with 0.01% w/v gelatin, 0.1% v/v t-octylphenoxypolyethoxyethanol, sold under the tradename Triton X-100 (Sigma Chemical Co., St. Louis, Mo.)), the needed nucleotide triphosphates, appropriate primers for amplifying the target sequence (0.5 $\mu$M) and Taq polymerase (available from Promega Corp., Madison, Wis.).

13. The carousel is rotated to close the chambers 250A–250C and the lower auxiliary block is positioned under the reaction chamber disk to provide more precise temperature control. The controller then initiates a temperature program modeled on the protocol described by Wu et al., *Proc. Natl. Acad. Sci. USA*, 86, 2752–2760 (1989). The program first heats the chambers 250A–250C to a temperature of 55° C. and maintains that temperature for 2 minutes. Next the controller cycles the temperature between a replication temperature of 72° C. (maintained for 3 minutes) and a DNA melting temperature of 94° C. (maintained for 1 minute). After the replication temperature incubation has been conducted 25 times, the material in the chambers 250A–250C is analyzed for the presence of the proper amplified sequence.

The eight (120H2), ninth (120I2), thirteenth (120M2) and fourteenth (120N2) fluid chambers are not used in this protocol and are available for post-reaction manipulations. Note that the sequence by which the carousel is rotated is designed so that no portion of the inner ring surface 140 that has been in contact with the nucleic acid-containing material rotates by the fluid exchange channels for the reaction chamber in which the negative control reaction is conducted. This precaution is desirable in view of the sensitivity of the PCR reaction to contamination. Fluid exchange channel 231D is situated so that when it is aligned with any fluid exchange port 121-A2 to 121-R2, none of fluid exchange channels 231A–231C and 232C is aligned. This lack of co-alignment between these two groups of reaction chambers prevents inadvertent mixing of fluids.

EXAMPLE 3
PCR Amplification

Recently it has been shown that paramagnetic DNA-binding beads can be used directly in the cell lysis stage to bind the DNA released from the lysed cells (e.g., uniform paramagnetic polystyrene beads sold under the tradename Dynabeads® DNA Direct™, available from Dynal, Lake Success, N.Y.). Accordingly, the protocol of Example 2 can be significantly simplified. In this example, each reaction chamber on the reaction chamber disk has a separate and independent set of fluid chambers and, if appropriate, a separate capillary tubing structure. For simplicity, the protocol outlined below focuses on one reaction chamber and its associated fluid chamber and capillary tubing structure. The protocol is as follows:

1. Capillary tubing structure 160 is aligned with chamber 250 of the assay cassette and a blood sample in the capillary tubing 150 is drawn into the fourth chamber 250 using air pressure. (The capillary tubing is filled with blood by aligning the outlet of the capillary tubing structure with a vent [not shown] located adjacent to fluid exchange channel 231 on the reaction chamber disk, and filling the capillary structure through inlet 151.) The blood sample only fills half the volume of the fourth reaction chamber. The chamber 250 is preloaded with a supply of paramagnetic, DNA-binding beads having a diameter of 50–100 $\mu$m (Dynal, Lake Success, N.Y.) and a volume of lysis solution equal to the volume of the sample is drawn. The lysis solution is a 2X solution of amplification buffer supplemented with 1.0% v/w Tween 20 (Sigma Chemical Co., St. Louis, Mo.). (The lysis solution can be substituted with the solution provided by Dynal.) To lock the lysis solution in place, the carousel is rotated to close the channel 231. The temperature of the chamber 250 is now maintained at 56° C.

2. After 45 minutes, the carousel is rotated to align the chamber 250 with first fluid chamber 120A, into which the lysis solution, which contains the cellular residue of the sample, is pushed. The DNA-binding beads, to which the cellular DNA is bound, remain in the chamber 250.

3. The carousel is rotated to align the chamber 250 with a second fluid chamber 120B, and wash solution composed of amplification buffer (40 mM NaCl, 20 mM Tris-HCl, pH 8.3, 5 mM MgSO$_4$) is introduced into the chamber 250. The carousel is then rotated to close the chamber 250. The DNA-binding beads are agitated magnetically.

4. After 10 minutes, the carousel is rotated to align the chamber 250 with the chamber 120B and the wash solution is pushed out of the reaction chambers.

5. Using a third fluid chamber 120C, steps 4 and 5 are repeated.

6. The carousel is then rotated to align the chamber 250 with a fourth fluid chamber 120D, from which is drawn an amplification solution containing amplification buffer (supplemented with 0.01% w/v gelatin, 0.1% v/v Triton X-100 (Sigma Chemical Co., St. Louis, Mo.)), the needed nucleotide triphosphates, appropriate primers for amplifying the target sequence (0.5 $\mu$M) and Taq polymerase (available from Promega Corp., Madison, Wis.).

7. The carousel is rotated to close the chamber 250 and the lower auxiliary block is positioned under the reaction chamber disk to provide more precise temperature control. The controller then initiates a temperature program modeled on the protocol described by Wu et al., *Proc. Natl. Acad. Sci. USA*, 86, 2752–2760 (1989). The program that first heats the chamber 250 to a temperature of 55° C. and maintains that temperature for 2 minutes. Next the controller cycles the temperature between an replication temperature of 72° C. (maintained for 3 minutes) and a DNA strand separation temperature of 94° C. (maintained for 1 minute). After the replication temperature incubation has been conducted 25 times, the material in the chamber 250 is analyzed for the presence of the proper amplified sequence.

While this invention has been described with an emphasis upon a preferred embodiment, it will be obvious to those of ordinary skill in the art that variations in the preferred composition and method may be used and that it is intended that the invention may be practiced otherwise than as specifically described herein. Accordingly, this invention includes all modifications encompassed within the spirit and scope of the invention as defined by the following claims.

The invention provides an economical, elevated temperature microreactor with effective valves suitable for use in conducting various forensic and diagnostic biochemical assays, such as, but not limited to, PCR assays. The microreactor is also suitably adapted for conducting automated assays even when high vapor pressure is not a particular concern.

The invention is also a system for conducting elevated temperature reactions in a fluid-tight manner within a reaction chamber comprising: (a) a first assembly comprising the reaction chamber, and (b) a second assembly for temperature control, wherein the second assembly can be positioned adjacent to the reaction chamber. The first assembly comprises a plurality of reaction chambers, each having a fluid exchange channel, and preferably comprises at least three of such reaction chambers. The second assembly comprises a heat source, a cooling sink, or both and preferably a fluid impeller.

The system can also include a third assembly that can be slideably positioned in contact with the first assembly and contains a plurality of fluid chambers, each fluid chamber having a fluid exchange port, a plurality of which fluid exchange ports can be aligned with the first fluid exchange channel by slideably positioning the third assembly relative to the first assembly and a first fluid impeller for impelling a fluid to flow from a fluid chamber having a fluid exchange port which can be aligned with the first fluid exchange channel into the reaction chamber of the aligned first fluid exchange channel; and in some embodiments, a second fluid impeller for impelling a fluid to leave the reaction chamber.

The first assembly fits within the third assembly, which combination is fluid-tight, wherein the first and third assemblies can slide relative to each other, such that fluid does not flow through the first fluid exchange channel when the first fluid exchange channel is not aligned with a fluid exchange channel in the third assembly. Further, the fluid-tight seal between the first assembly and the third assembly is effective in retaining a fluid in the reaction chamber when the temperature of the fluid is at about 90° C. to about 100° C.

Another embodiment includes at least one reaction or fluid chamber that has an external transparent wall. The invention also comprises a light source capable of directing light to the external transparent wall of the reaction or fluid chamber. Such an embodiment includes a light detection device capable of detecting (a) the light reflected from an illuminated reaction or fluid chamber having the external transparent wall, (b) the light transmitted through an illuminated reaction or fluid chamber having the external transparent wall, or (c) the light emissions emanating from an excited molecule in a reaction or fluid chamber having the external transparent wall.

Another embodiment includes a slider for sliding the third assembly or the first assembly and a processor for controlling: (a) the sliding of the third assembly or the first assembly, and (b) a first fluid impeller for impelling fluid to flow from a fluid chamber to a reaction chamber. The slider effects linear or circular movement between the first and third assemblies.

The invention also can include a temperature monitoring device for monitoring the temperature of the reaction chamber. Other embodiments include a processor for receiving a signal from the temperature monitoring device and controlling the heat source. The cooling sink used in the context of the present invention can also be under the control of the processor. The cooling sink comprises conduits containing a circulating fluid.

Another embodiment includes a permanent magnet that can be positioned adjacent to the reaction chamber, a rotator for rotating the permanent magnet, a slider for sliding the first or third assembly, and a processor for controlling: (a) the sliding of the first assembly or the third assembly, (b) the first fluid impeller for impelling fluid to flow from a fluid chamber to a reaction chamber, (c) the heat source, and (d) the rotation of the magnet.

Another embodiment relates to a method of conducting a PCR reaction comprising introducing a sample into a first reaction chamber of the assay system described herein and transferring from one or more fluid chambers to the first reaction chamber solutions containing reagents necessary for conducting the PCR reaction. Preferably, the second assembly of the assay system raises the temperature from about 25° C. to about 75° C. within about 5 seconds; the second assembly also preferably lowers the temperature from about 75° C. to about 50° C. within about 5 seconds.

The invention includes a mechanism for rapidly adjusting the temperature of a reaction chamber, the assay system comprising: (i) a first assembly comprising a reaction chamber having a first and a second cover and a thickness defined by the distance between the first and second covers, (ii) a second assembly comprising a heat source, a cooling sink, and a plurality of pressurized fluid channels that open on the surface of the second assembly, and (iii) a pressure controller for controlling the fluid pressure within the pressurized fluid channels; wherein the second assembly can be positioned adjacent to the reaction chamber such that the pressurized fluid channels are in contact with a cover of the reaction chamber. The heat source included in the second assembly preferably comprises at least one electrical heater attached to the second assembly. The cooling sink included in the second assembly preferably comprises a conduit for water or other fluid integral to the second assembly and a fluid impeller for causing fluid to flow through the conduit.

Preferably, the first and third assemblies are used in combination with a second assembly, which comprises (i) first and second end plates, wherein the first end plate can be positioned adjacent to the reaction chamber and (ii) a plurality of paired p-type and n-type semiconductor blocks positioned between the first and second end-plates and electrically connected in series to form a thermoelectric heat pump. The heat pump pumps heat from the first end plate to the second end plate when a voltage with a first polarity is applied across the serially connected semiconductor blocks and from the second end to the first end plate when a voltage of the polarity opposite the first polarity is applied across the serially connected semiconductor blocks. Preferably, the reaction chamber thickness is about 1 mm or less.

A preferred embodiment is used when a fluid in the pressurized fluid channels has elevated pressure and the second assembly is positioned adjacent to the reaction chamber, pressure is applied to the adjacent surface of the reaction chamber. This use is preferably facilitated when the first cover is formed of a deformable material and wherein, when the second assembly is positioned adjacent to the first cover, gaseous pressure applied against the first cover via the plurality of adjacent passageways is effective to deform the first cover so as to narrow the width of the reaction chamber. Thus, when the second assembly is positioned adjacent to the first cover and when a fluid in the pressurized fluid channels of the second assembly has reduced pressure, the first cover adheres to the second assembly. The invention also preferably comprises a translocator for moving the second assembly away from the first assembly, wherein when the first cover is adhered to the second assembly, the second assembly can be moved away from the first assembly by moving the second assembly away from the first assembly.

A preferred embodiment comprises (a) a reaction chamber having a cover formed of a deformable material and (b) a mechanism for rapidly adjusting the temperature of the reaction chamber, which mechanism comprises: (i) first and second end plates, wherein the first end plate can be positioned in contact with the reaction chamber cover; and (ii) a plurality of paired p-type and n-type semiconductor blocks positioned between the first and second end-plates and electrically connected in series to form a thermoelectric heat pump; wherein the heat pump pumps heat from the first end plate to the second end plate when a current with a first polarity is applied across the serially connected semiconductor blocks and from the second end to the first end plate when a current of the polarity opposite the first polarity is applied across the serially connected semiconductor blocks.

We claim:

1. An assay system for conducting elevated temperature reactions in a fluid-tight manner within an enclosed reaction chamber, the assay system comprising: (a) a first assembly comprising the reaction chamber and a first fluid exchange channel that provides fluid communication to and from the reaction chamber, (b) a second assembly for temperature control, wherein the second assembly is positioned adjacent to the reaction chamber; and (c) a third assembly that is slidably positioned in contact with the first assembly and contains a plurality of fluid chambers, wherein the first assembly fits within the third assembly in a fluid-tight, slidable manner such that fluid does not flow through the first fluid exchange channel when the first fluid exchange channel is not aligned with a fluid exchange channel in the third assembly, the fluid chambers having fluid exchange ports, a plurality of which fluid exchange ports can be aligned with the first fluid exchange channel by sidably positioning the third assembly relative to the first assembly, wherein a particular fluid chamber can be in fluid communication with the reaction chamber.

2. The assay system of claim 1, further comprising, positioned to interact with the third assembly, a first fluid impeller for impelling a fluid to flow from a fluid chamber having a fluid exchange port which can be aligned with the first fluid exchange channel into the reaction chamber of the aligned first fluid exchange channel.

3. The assay system of claim 2, further comprising a slider for sliding the third assembly or the first assembly and a processor for controlling: (a) the sliding of the third assembly or the first assembly, and (b) the first fluid impeller.

4. The assay system of claim 3, wherein the slider effects linear or circular movement between the first and third assemblies.

5. The assay system of claim 2, wherein the second assembly comprises a heat source, and further comprising a magnet positioned adjacent to the reaction chamber, a rotator, on which the magnet is mounted, for rotating the magnet, a slider, operatively linked to the first or third assembly, for sliding the first or third assembly, and a processor for controlling: (a) the sliding of the first assembly or the third assembly, (b) the first fluid impeller, (c) the heat source, and (d) the rotation of the magnet.

6. A method of conducting a PCR reaction comprising (a) introducing a sample into a first reaction chamber of the assay system of claim 2 and transferring from one or more fluid chambers to the first reaction chamber solutions containing reagents necessary for conducting the PCR reaction and (b) cycling the temperature to achieve cycles of nucleic acid amplification.

7. The method of claim 6, wherein the second assembly raises the temperature from about 25° C. to about 75° C. within about 5 seconds.

8. The method of claim 6, wherein the second assembly lowers the temperature from about 75° C. to about 50° C. within about 5 seconds.

9. The assay system of claim 1, further comprising, positioned to interact with the first assembly, a second fluid impeller for, when the fluid excbage port of a fluid chamber is aligned with the first fluid exchange channel, impelling a fluid to flow from the reaction chamber through the first fluid exchange channel and the aligned fluid exchange port into that fluid chamber.

10. The assay system of claim 1, wherein the fluid-tight seal between the first assembly and the third assembly is effective in retaining a fluid in the reaction chamber when the temperature of the fluid is at about 90° C. to about 100° C.

11. The assay system of claim 1, wherein at least one reaction or fluid chamber has an external transparent wall.

12. The assay system of claim 11, further comprising a light source capable of directing light to the external transparent wall of the reaction or fluid chamber.

13. The assay system of claim 12, further comprising a light detection device capable of detecting (a) the light reflected from an illuminated reaction or fluid chamber having the external transparent wall, (b) the light transmitted through an illuminated reaction or fluid chamber having the external transparent wall, or (c) the light emissions emanating from an excited molecule in a reaction or fluid chamber having the external transparent wall.

14. The assay system of claim 1, wherein the second assembly comprises a heat source, a cooling sink, or both.

15. The assay system of claim 14, further comprising a temperature monitoring device for monitoring the temperature of the reaction chamber operatively connected to the second assembly.

16. The assay system of claim 15, further comprising a processor for receiving a signal from the temperature monitoring device and for controlling the heat source operatively connected to the temperature monitoring device.

17. The assay system of claim 16, wherein the cooling sink is under the control of the processor.

18. The assay system of claim 17, wherein the cooling sink comprises conduits containing a circulating fluid and an impeller for causing said fluid to circulate.

19. The assay system of claim 1, wherein the first component comprises a plurality of reaction chambers, each having a fluid exchange channel.

20. The assay system of claim 19, wherein the first component comprises at least about 3 reaction chambers.

21. An system for conducting chemical assays having a mechanism for adjusting the temperature of a reaction chamber, the assay system comprising: (a) a first assembly comprising an enclosed reaction chamber having a upper and a lower cover and a thickness defined by the distance between the upper and lower covers, wherein at least the upper cover is formed of a deformable material, (b) a second assembly comprising a heat source, a cooling sink, and a plurality of pressurized fluid channels that open on the surface of the second component assembly, wherein the second assembly is positioned adjacent to the reaction chamber, wherein the reaction chamber further comprises at least one sealable entry port and (c) a pressure controller operatively linked to the pressurized fluid channels, for controlling gas pressure within the pressurized fluid channels; wherein the second assembly can be positioned adjacent to the reaction chamber such that the pressurized fluid channels are in contact with the upper cover of the reaction chamber, and wherein elevated gas pressure can be channeled through the pressurized fluid channels to impact the upper cover and thereby push the upper cover towards the lower cover so as to narrow the width of the reaction chamber.

22. The assay system of claim 21, wherein the heat source comprises at least one electrical heater attached to the second assembly.

23. The assay system of claim 21, wherein the cooling sink comprises a conduit for water or other fluid integral to the second assembly and a fluid impeller for causing fluid to flow through the conduit.

24. The assay system of claim 21, wherein the second assembly comprises: (a) first and second end plates, wherein the first end plate can be positioned adjacent to the reaction chamber, and (b) a plurality of paired p-type and n-type semiconductor blocks positioned between the first and second end-plates and electrically connected in series to form a thermoelectric heat punp, wherein the heat pump pumps heat from the first end plate to the second end plate when a voltage with a first polarity is applied across the serially connected semiconductor blocks and from the second end to the first end plate when a voltage of the polarity opposite the first polarity is applied across the serially connected semiconductor blocks.

25. The assay system of claim 21, wherein the reaction chamber thickness is about 1 mm or less.

26. The assay system of claim 21, wherein, when the second component is positioned adjacent to the upper cover and when a fluid in the pressurized fluid channels of the upper assembly has reduced pressure, the first cover adheres to the second assembly.

27. The assay system of claim 26, further comprising a translocator for moving the second assembly away from the upper assembly, wherein when the first cover is adhered to the second assembly, the second assembly can be moved away from the first assembly.

* * * * *